United States Patent [19]

Kraus et al.

[11] Patent Number: 5,820,859
[45] Date of Patent: Oct. 13, 1998

[54] METHOD OF TARGETING A THERAPEUTIC AGENT TO CELLS EXPRESSING THE ERB B-3 RECEPTOR

[75] Inventors: Matthias H. Kraus, Bethesda, Md.; Stuart A. Aaronson, Vienna, Va.

[73] Assignee: The United States of America as represented by the Department of Health and Human Services, Washington, D.C.

[21] Appl. No.: 473,119

[22] Filed: Jun. 7, 1995

Related U.S. Application Data

[60] Division of Ser. No. 978,895, Nov. 10, 1992, Pat. No. 5,480,968, which is a continuation-in-part of Ser. No. 444,406, Dec. 1, 1989, Pat. No. 5,183,884.

[51] Int. Cl.$^6$ .................... A61K 39/395; C07K 16/30
[52] U.S. Cl. .................... 424/143.1; 424/138.1; 424/139.1; 424/181.1; 424/183.1
[58] Field of Search .............. 424/138.1, 139.1, 424/143.1, 152.1, 179.1, 181.1; 530/387.7, 388.8, 388.22, 389.7, 391.7, 350, 397

[56] References Cited

U.S. PATENT DOCUMENTS

| | | | |
|---|---|---|---|
| 4,480,968 | 11/1984 | Kraus et al. | 530/326 |
| 5,183,884 | 2/1993 | Kraus et al. | 536/23.5 |

OTHER PUBLICATIONS

Drebin et al., Monoclonal antibodies specific for the neu oncogene product directly mediate anti–tumor effects in vivo, Oncogene, 2:3878–394, 1988.

Primary Examiner—Stephen Walsh
Assistant Examiner—Claire M. Kaufman
Attorney, Agent, or Firm—Needle & Rosenburg, PC

[57] ABSTRACT

A DNA fragment distinct from the epidermal growth factor receptor (EGFR) and erbB-2 genes was detected by reduced stringency hybridization of v-erbB to normal genomic human DNA. cDNA cloning revealed a predicted 148 kd transmembrane polypeptide with structural features identifying it as a member of the erbB family, prompting designation of the new gene as erbB-3. It was mapped to human chromosome 12q11–13 and was shown to be expressed as a 6.2 kb transcript in a variety of normal tissues of epithelial origin. Markedly elevated erbB-3 mRNA levels were demonstrated in certain human mammary tumor cell lines. These findings indicate that increased erbB-3 expression, as in the case of EGFR and erbB-2, plays a role in some human malignancies. Using erbB-3 specific antibodies (polyclonal or monoclonal), the erbB-3 protein was identified as a 180 kDa glycoprotein, gp180$^{erbB-3}$. The intrinsic catalytic function of gp180$^{erbB-3}$ was uncovered by its ability to autophosphorylate in vitro. Ligand-dependent signaling of its cytoplasmic domain was established employing transfectants which express a chimeric EGFR/erbB-3 protein, gp180$^{EGFR/erbB-3}$. EGF induced tyrosine phosphorylation of the chimera and promoted soft agar colony formation of such transfectants. These findings, combined with the detection of constitutive tyrosine phosphorylation of gp180$^{erbB-3}$ in 4 out of 12 human mammary tumor cell lines, implicate the activated erbB-3 product in the pathogenesis of some human malignancies. Thus, this invention also relates to procedures for targeting a therapeutic drug to cells having a high level of the receptor protein.

2 Claims, 14 Drawing Sheets

FIGURE 3 (SEQ ID NO:1)

```
GAATTCCAGA TCTCAGTGAC TGATTCCCCC AACCTTAAGA ATACTTTCTT CCCCTATACC  60

TACAG GGA ATG TAC TAC CTT GAG GAA CAT GGT ATG GTG CAT AGA AAC     107
      Gly Met Tyr Tyr Leu Glu Glu His Gly Met Val His Arg Asn

CTG GCT GCC CGA AAC GTG CTA CTC AAG TCA CCC AGT CAG GTT CAG GTG   155
Leu Ala Ala Arg Asn Val Leu Leu Lys Ser Pro Ser Gln Val Gln Val

GCA GAT TTT GGT GTG GCT GAC CTG CTG CCT CCT GAT GAT AAG CAG CTG   203
Ala Asp Phe Gly Val Ala Asp Leu Leu Pro Pro Asp Asp Lys Gln Leu

CTA TAC AGT GAG GCC AAG GTGAGGAGAC ACAAAGGGTA AGGAGGCGGG          251
Leu Tyr Ser Glu Ala Lys

GGTGGAGTGA AGCATGGGGA TAGGGAGCAG CCAGTGGTCT CTTCCAGAGG CAAGCAGATG 311
CTTCATGGTA AGTTCAAGGA GAGAAGGCTG CAGATGCCAG ATATTTTAGT TCAGAGGGCA 371
ACAAAGAAAA TAATGATCAA GAACTTGGGA CTGGCCGGGC GCGGTGGCTC ACGCCTGTAA 431
TCCCAACACT TCGGGAGGCC AAGGCGGGTG GATCACAAGG TCAGGAGATC AAGACCATCC 491
TGGCTAGCAC GGTGAAACCC CGTCTCTACT AAATATACAA AAAAAAAAA ATTAGCCAGG  551
CGTGGCGGCA TGCATCTGTA CTCCCAGCTA CTCGGGAGGC TGAGGCAGGA GAATGGCGTG 611
AACCCAGGAG GCGGAGCTTG CAGTGGGCCG AGATCGCACC ACTGCACTCC AGTCTGGGCG 671
ACAGAGCGAG ACTCCGTCTC AAAAAAAAAA AAAAAAGAAT TTGGGACTTG GAAATCCTAA 731
GAAAATTTGT GGAAATAAAC TTGTGATACC TCTATCTTTA ATCCGCAG ACT CCA ATT 788
                                                   Thr Pro Ile

AAG TGG ATG GCC CTT GAG AGT ATC CAC TTT GGG AAA TAC ACA CAC CAG  836
Lys Trp Met Ala Leu Glu Ser Ile His Phe Gly Lys Tyr Thr His Gln

AGT GAT GTC TGG AGC TAT G GTCAGTGCAT CTGGATGCCC TCTCTACCAT        885
Ser Asp Val Trp Ser Tyr

CACTGGCCCC AGTTTCAAAT TTACCTTTTG AGAGCCCCCT CTTAGAATCT CTAAGCACTT 945
CAGATTTTTG TGTTAGATCA GGTTCTGCCT TCCCTTCACT TCATGCCCAT GTCTACTATT 1005
TTGCCAGTGA CTAGTCCATG TCTTCCTGCA ACAG GT GTG ACA GTT TGG GAG     1056
                                    Gly Val Thr Val Trp Glu

TTG ATG ACC TTC GGG GCA GAG CCC TAT GCA GGG CTA CGA TTG GCT GAA  1104
Leu Met Thr Phe Gly Ala Glu Pro Tyr Ala Gly Leu Arg Leu Ala Glu

GTA CCA GAC CTG CTA GAG AAG GGG GAG CGG TTG GCA CAG CCC CAG ATC  1152
Val Pro Asp Leu Leu Glu Lys Gly Glu Arg Leu Ala Gln Pro Gln Ile

TGC ACA ATT GAT GTC TAC ATG GTG ATG GTC AAG TGTGAGTTAC CTGCTGAGCC 1205
Cys Thr Ile Asp Val Tyr Met Val Met Val Lys

CAACCATTTT CTCTTTTTTT CTTTTTTTTT CTTTTTTTTT TTTTTTGAG ACAGAGTCTC  1265
ACAATTGTCA CCCAGGCTGG AGTGCAATGG TGCAATCAAT CTTGGCTCAC TACAACCTCC 1325
GCCTCTCGGG TTCAAGAGAT TCTCCTGCTT CAGCTCCGGA GTAGCTGGGA TTACAGCGCC 1385
CGCCACACCT GGATAACTGT TACACTTTTA GTAGAGATGG GGTTTCACCA TGTTGGCCAG 1445
GCTGGTCTCA AACTCCTGAC CTCAGGTGAT CCGCCTGCCT CAGCTTCCCA AAGTGCTGGG 1505
ATTACAGGTG TGAGCCATCA TGCTCGCCTG ACTGCAG                         1542
```

```
MRANDALQVL GLLFSLARGS EVGNSQAVCP GTLNGLSVTG DAENQYQTLY KLYERCEVVM GNLEIVLTGH    70

NADLSFLQWI REVTGYVLVA MNEFSTLPLP NLRVVRGTQV YDGKFAIFVM LNYNTNSSHA LRQLRLTQLT   140

EILSGGVYIE KNDKLCHMDT IDWRDIVRDR DAEIVVKDNG RSCPPCHEVC KGRCWGPCSE DCQTLTKTIC   210

APQCNGHCFG PNPNQCCHDE CAGGCSGPQD TDCFACRHFN DSGACVPRCP QPLVYNKLTF QLEPNPHTKY   280

QYGGVCVASC PHNFVVDQTS CVRACPPDKM EVDKNGLKMC EPCGGLCPKA CEGTGSGSRF QTVDSSNIDG   350

FVNCTKILGN LDFLITGLNG DPWHKIPALD PEKLNVFRTV REITGYLNIQ SWPPHMHNFS VFSNLTTIGG   420

RSLYNRGFSL LIMKNLNVTS LGFRSLKEIS AGRIYISANR QLCYHHSLNW TKVLRGPTEE RLDIKHNRPR   490

RDCVAEGKVC DPLCSSGGCW GPGPGQCLSC RNYSRGGVCV THCNFLNGEP REFAHEAECF SCHPECQPME   560

GTATCNGSGS DTCAQCAHFR DGPHCVSSCP HGVLGAKGPI YKYPDVQNEC RPCHENCTQG CKGPELQDCL   630

GQTLVLIGKT HLTMALTVIA GLVVIFMMLG CTFLYWRGRR IQNKRAMRRY LERGESIEPL DPSEKANKVL   700

ARIFKETELR KLKVLGSGVF GTVHKGVWIP EGESIKIPVC IKVIEDKSGR QSFQAVTDHM LAIGSLDHAH   770

IVRLLGLCPG SSLQLVTQYL PLGSLLDHVR QHRGALGPQL LLNWGVQIAK GMYYLEEHGM VHRNLAARNV   840

LLKSPSQVQV ADFGVADLLP PDDKQLLYSE AKTPIKWMAL ESIHFGKYTH QSDVWSYGVT VWELMTFGAE   910

PYAGLRLAEV PDLLEKGERL AQPQICTIDV YMVMVKCWMI DENIRPTFKE LANEFTRMAR DPPRYLVIKR   980

ESGPGIAPGP EPHGLTNKKL EEVELEPELD LDLDLEAEED NLATTTLGSA LSLPVGTLNR PRGSQSLLSP  1050

SSGYMPMNQG NLGESCQESA VSGSSERCPR PVSLHPMPRG CLASESSEGH VTGSEAELQE KVSMCRSRSR  1120

SRSPRPRGDS AYHSQRHSLL TPVTPLSPPG LEEEDVNGYV MPDTHLKGTP SSREGTLSSV GLSSVLGTEE  1190

EDEDEEYEYM NRRRRHSPPH PPRPSSLEEL GYEYMDVGSD LSASLGSTQS CPLHPVPIMP TAGTTPDEDY  1260

EYMNRQRDGG GPGGDYAAMG ACPASEQGYE EMRAFQGPGH QAPHVHYARL KTLRSLEATD SAFDNPDYWH  1330

SRLFPKANAQ RT                                                                1342
```

FIG.4A (SEQ ID NO:4)

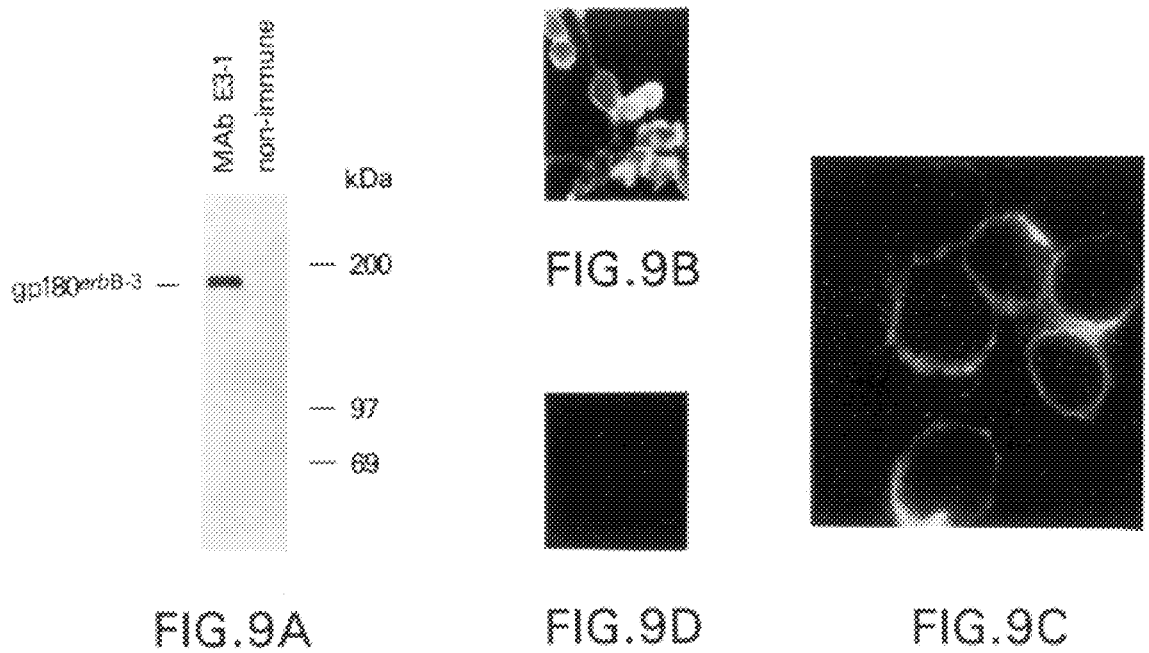

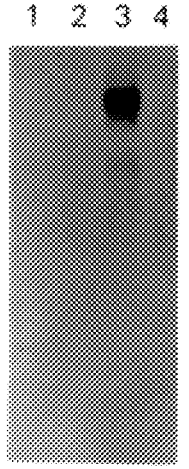
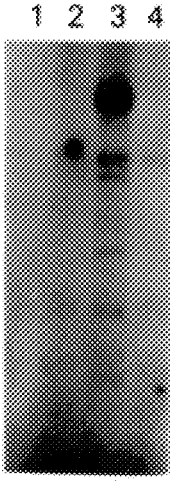
FIG.10A  FIG.10B  FIG.10C ced by mechanisms involving overexpression or mutations that constitutively activate the catalytic activity, of their encoded receptor proteins (Bargmann, C. I., Hung, M. C. & Weinberg, R. A., 1986, *Cell* 45:649–657; Di Fiore, P. P., Pierce, J. H., Kraus, M. H., Segatto. O., King, C. R. & Aaronson, S. A., 1987, *Science* 237:178–182; Di Fiore, P. P., Pierce, J. H., Fleming, T. P., Hazan, R., Ullrich, A., King, C. R., Schlessinger, J. & Aaronson, S. A., 1987, *Cell*

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 1542 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: exon
        ( B ) LOCATION: 66..221

( i x ) FEATURE:
        ( A ) NAME/KEY: exon
        ( B ) LOCATION: 780..855

( i x ) FEATURE:
        ( A ) NAME/KEY: exon
        ( B ) LOCATION: 1040..1185

( i x ) FEATURE:
        ( A ) NAME/KEY: intron
        ( B ) LOCATION: 222..779

( i x ) FEATURE:
        ( A ) NAME/KEY: intron
        ( B ) LOCATION: 856..1039

( i x ) FEATURE:
        ( A ) NAME/KEY: CDS
        ( B ) LOCATION: join(66..221, 780..855, 1040..1185)

( x i ) SEQUENCE DESCRIPTION: SEQ ID NO:1:

```
GAATTCCAGA  TCTCAGTGAC  TGATTCCCCC  AACCTTAAGA  ATACTTTCTT  CCCCTATACC           60

TACAG  GGA  ATG  TAC  TAC  CTT  GAG  GAA  CAT  GGT  ATG  GTG  CAT  AGA  AAC          107
       Gly  Met  Tyr  Tyr  Leu  Glu  Glu  His  Gly  Met  Val  His  Arg  Asn
        1              5                           10

CTG  GCT  GCC  CGA  AAC  GTG  CTA  CTC  AAG  TCA  CCC  AGT  CAG  GTT  CAG  GTG     155
Leu  Ala  Ala  Arg  Asn  Val  Leu  Leu  Lys  Ser  Pro  Ser  Gln  Val  Gln  Val
 15                  20                           25                       30

GCA  GAT  TTT  GGT  GTG  GCT  GAC  CTG  CTG  CCT  CCT  GAT  GAT  AAG  CAG  CTG     203
Ala  Asp  Phe  Gly  Val  Ala  Asp  Leu  Leu  Pro  Pro  Asp  Asp  Lys  Gln  Leu
                     35                           40                       45

CTA  TAC  AGT  GAG  GCC  AAG  GTGAGGAGAC  ACAAAGGGTA  AGGAGGCGGG                    251
Leu  Tyr  Ser  Glu  Ala  Lys
```

```
                     50
GGTGGAGTGA  AGCATGGGGA  TAGGGAGCAG  CCAGTGGTCT  CTTCCAGAGG  CAAGCAGATG       311

CTTCATGGTA  AGTTCAAGGA  GAGAAGGCTG  CAGATGCCAG  ATATTTTAGT  TCAGAGGGCA       371

ACAAAGAAAA  TAATGATCAA  GAACTTGGGA  CTGGCCGGGC  GCGGTGGCTC  ACGCCTGTAA       431

TCCCAACACT  TCGGGAGGCC  AAGGCGGGTG  GATCACAAGG  TCAGGAGATC  AAGACCATCC       491

TGGCTAGCAC  GGTGAAACCC  CGTCTCTACT  AAATATACAA  AAAAAAAAA   ATTAGCCAGG       551

CGTGGCGGCA  TGCATCTGTA  CTCCCAGCTA  CTCGGGAGGC  TGAGGCAGGA  GAATGGCGTG       611

AACCCAGGAG  GCGGAGCTTG  CAGTGGGCCG  AGATCGCACC  ACTGCACTCC  AGTCTGGGCG       671

ACAGAGCGAG  ACTCCGTCTC  AAAAAAAAAA  AAAAAAGAAT  TTGGGACTTG  GAAATCCTAA       731

GAAAATTTGT  GGAAATAAAC  TTGTGATACC  TCTATCTTTA  ATCCGCAG ACT CCA ATT         788
                                                         Thr Pro Ile
                                                                  55

AAG TGG ATG GCC CTT GAG AGT ATC CAC TTT GGG AAA TAC ACA CAC CAG              836
Lys Trp Met Ala Leu Glu Ser Ile His Phe Gly Lys Tyr Thr His Gln
             60                  65                      70

AGT GAT GTC TGG AGC TAT  G GTCAGTGCAT CTGGATGCCC TCTCTACCAT                  885
Ser Asp Val Trp Ser Tyr
                 75

CACTGGCCCC  AGTTCAAAT   TTACCTTTTG  AGAGCCCCT   CTTAGAATCT  CTAAGCACTT       945

CAGATTTTTG  TGTTAGATCA  GGTTCTGCCT  TCCCTTCACT  TCATGCCCAT  GTCTACTATT      1005

TTGCCAGTGA  CTAGTCCATG  TCTTCCTGCA  ACAG GT GTG ACA GTT TGG GAG             1056
                                         Gly Val Thr Val Trp Glu
                                                          80

TTG ATG ACC TTC GGG GCA GAG CCC TAT GCA GGG CTA CGA TTG GCT GAA             1104
Leu Met Thr Phe Gly Ala Glu Pro Tyr Ala Gly Leu Arg Leu Ala Glu
         85                   90                  95

GTA CCA GAC CTG CTA GAG AAG GGG GAG CGG TTG GCA CAG CCC CAG ATC             1152
Val Pro Asp Leu Leu Glu Lys Gly Glu Arg Leu Ala Gln Pro Gln Ile
100                  105                 110                 115

TGC ACA ATT GAT GTC TAC ATG GTG ATG GTC AAG TGTGAGTTAC CTGCTGAGCC           1205
Cys Thr Ile Asp Val Tyr Met Val Met Val Lys
                 120                 125

CAACCATTTT  CTCTTTTTTT  CTTTTTTTTT  CTTTTTTTTT  TTTTTTGAG   ACAGAGTCTC      1265

ACAATTGTCA  CCCAGGCTGG  AGTGCAATGG  TGCAATCAAT  CTTGGCTCAC  TACAACCTCC      1325

GCCTCTCGGG  TTCAAGAGAT  TCTCCTGCTT  CAGCTCCGGA  GTAGCTGGGA  TTACAGCGCC      1385

CGCCACACCT  GGATAACTGT  TACACTTTTA  GTAGAGATGG  GGTTTCACCA  TGTTGGCCAG      1445

GCTGGTCTCA  AACTCCTGAC  CTCAGGTGAT  CCGCCTGCCT  CAGCTTCCCA  AAGTGCTGGG      1505

ATTACAGGTG  TGAGCCATCA  TGCTCGCCTG  ACTGCAG                                 1542
```

( 2 ) INFORMATION FOR SEQ ID NO:2:

( i ) SEQUENCE CHARACTERISTICS:
        ( A ) LENGTH: 126 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Gly Met Tyr Tyr Leu Glu Glu His Gly Met Val His Arg Asn Leu Ala
 1               5                  10                  15

Ala Arg Asn Val Leu Leu Lys Ser Pro Ser Gln Val Gln Val Ala Asp
                 20                  25                  30
```

```
Phe  Gly  Val  Ala  Asp  Leu  Leu  Pro  Pro  Asp  Asp  Lys  Gln  Leu  Leu  Tyr
          35                      40                 45

Ser  Glu  Ala  Lys  Thr  Pro  Ile  Lys  Trp  Met  Ala  Leu  Glu  Ser  Ile  His
     50                      55                 60

Phe  Gly  Lys  Tyr  Thr  His  Gln  Ser  Asp  Val  Trp  Ser  Tyr  Gly  Val  Thr
65                       70                      75                          80

Val  Trp  Glu  Leu  Met  Thr  Phe  Gly  Ala  Glu  Pro  Tyr  Ala  Gly  Leu  Arg
               85                      90                           95

Leu  Ala  Glu  Val  Pro  Asp  Leu  Leu  Glu  Lys  Gly  Glu  Arg  Leu  Ala  Gln
               100                      105                     110

Pro  Gln  Ile  Cys  Thr  Ile  Asp  Val  Tyr  Met  Val  Met  Val  Lys
          115                      120                     125
```

( 2 ) INFORMATION FOR SEQ ID NO:3:

( i ) SEQUENCE CHARACTERISTICS:
        ( A ) LENGTH: 4905 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 100..4125

( x i ) SEQUENCE DESCRIPTION: SEQ ID NO:3:

```
ACCAATTCGC  CAGCGGTTCA  GGTGGCTCTT  GCCTCGATGT  CCTAGCCTAG  GGGCCCCCGG        60

GCCGGACTTG  GCTGGGCTCC  CTTCACCCTC  TGCGGAGTC  ATG  AGG  GCG  AAC  GAC       114
                                               Met  Arg  Ala  Asn  Asp
                                                1                     5

GCT  CTG  CAG  GTG  CTG  GGC  TTG  CTT  TTC  AGC  CTG  GCC  CGG  GGC  TCC  GAG    162
Ala  Leu  Gln  Val  Leu  Gly  Leu  Leu  Phe  Ser  Leu  Ala  Arg  Gly  Ser  Glu
               10                      15                      20

GTG  GGC  AAC  TCT  CAG  GCA  GTG  TGT  CCT  GGG  ACT  CTG  AAT  GGC  CTG  AGT    210
Val  Gly  Asn  Ser  Gln  Ala  Val  Cys  Pro  Gly  Thr  Leu  Asn  Gly  Leu  Ser
               25                      30                      35

GTG  ACC  GGC  GAT  GCT  GAG  AAC  CAA  TAC  CAG  ACA  CTG  TAC  AAG  CTC  TAC    258
Val  Thr  Gly  Asp  Ala  Glu  Asn  Gln  Tyr  Gln  Thr  Leu  Tyr  Lys  Leu  Tyr
               40                      45                      50

GAG  AGG  TGT  GAG  GTG  GTG  ATG  GGG  AAC  CTT  GAG  ATT  GTG  CTC  ACG  GGA    306
Glu  Arg  Cys  Glu  Val  Val  Met  Gly  Asn  Leu  Glu  Ile  Val  Leu  Thr  Gly
     55                      60                      65

CAC  AAT  GCC  GAC  CTC  TCC  TTC  CTG  CAG  TGG  ATT  CGA  GAA  GTG  ACA  GGC    354
His  Asn  Ala  Asp  Leu  Ser  Phe  Leu  Gln  Trp  Ile  Arg  Glu  Val  Thr  Gly
70                       75                      80                          85

TAT  GTC  CTC  GTG  GCC  ATG  AAT  GAA  TTC  TCT  ACT  CTA  CCA  TTG  CCC  AAC    402
Tyr  Val  Leu  Val  Ala  Met  Asn  Glu  Phe  Ser  Thr  Leu  Pro  Leu  Pro  Asn
               90                      95                     100

CTC  CGC  GTG  GTG  CGA  GGG  ACC  CAG  GTC  TAC  GAT  GGG  AAG  TTT  GCC  ATC    450
Leu  Arg  Val  Val  Arg  Gly  Thr  Gln  Val  Tyr  Asp  Gly  Lys  Phe  Ala  Ile
               105                     110                     115

TTC  GTC  ATG  TTG  AAC  TAT  AAC  ACC  AAC  TCC  AGC  CAC  GCT  CTG  CGC  CAG    498
Phe  Val  Met  Leu  Asn  Tyr  Asn  Thr  Asn  Ser  Ser  His  Ala  Leu  Arg  Gln
               120                     125                     130

CTC  CGC  TTG  ACT  CAG  CTC  ACC  GAG  ATT  CTG  TCA  GGG  GGT  GTT  TAT  ATT    546
Leu  Arg  Leu  Thr  Gln  Leu  Thr  Glu  Ile  Leu  Ser  Gly  Gly  Val  Tyr  Ile
     135                     140                     145

GAG  AAG  AAC  GAT  AAG  CTT  TGT  CAC  ATG  GAC  ACA  ATT  GAC  TGG  AGG  GAC    594
Glu  Lys  Asn  Asp  Lys  Leu  Cys  His  Met  Asp  Thr  Ile  Asp  Trp  Arg  Asp
150                     155                     160                         165
```

| | | | | | | | | | | | | | | | | |
|---|---|---|---|---|---|---|---|---|---|---|---|---|---|---|---|---|
| ATC | GTG | AGG | GAC | CGA | GAT | GCT | GAG | ATA | GTG | GTG | AAG | GAC | AAT | GGC | AGA | 642 |
| Ile | Val | Arg | Asp | Arg | Asp | Ala | Glu | Ile | Val | Val | Lys | Asp | Asn | Gly | Arg | |
| | | 170 | | | | | | 175 | | | | | | 180 | | |
| AGC | TGT | CCC | CCC | TGT | CAT | GAG | GTT | TGC | AAG | GGG | CGA | TGC | TGG | GGT | CCT | 690 |
| Ser | Cys | Pro | Pro | Cys | His | Glu | Val | Cys | Lys | Gly | Arg | Cys | Trp | Gly | Pro | |
| | | | 185 | | | | | | 190 | | | | | | 195 | |
| GGA | TCA | GAA | GAC | TGC | CAG | ACA | TTG | ACC | AAG | ACC | ATC | TGT | GCT | CCT | CAG | 738 |
| Gly | Ser | Glu | Asp | Cys | Gln | Thr | Leu | Thr | Lys | Thr | Ile | Cys | Ala | Pro | Gln | |
| | | | 200 | | | | | 205 | | | | | 210 | | | |
| TGT | AAT | GGT | CAC | TGC | TTT | GGG | CCC | AAC | CCC | AAC | CAG | TGC | TGC | CAT | GAT | 786 |
| Cys | Asn | Gly | His | Cys | Phe | Gly | Pro | Asn | Pro | Asn | Gln | Cys | Cys | His | Asp | |
| | | 215 | | | | | 220 | | | | | 225 | | | | |
| GAG | TGT | GCC | GGG | GGC | TGC | TCA | GGC | CCT | CAG | GAC | ACA | GAC | TGC | TTT | GCC | 834 |
| Glu | Cys | Ala | Gly | Gly | Cys | Ser | Gly | Pro | Gln | Asp | Thr | Asp | Cys | Phe | Ala | |
| 230 | | | | | 235 | | | | | 240 | | | | | 245 | |
| TGC | CGG | CAC | TTC | AAT | GAC | AGT | GGA | GCC | TGT | GTA | CCT | CGC | TGT | CCA | CAG | 882 |
| Cys | Arg | His | Phe | Asn | Asp | Ser | Gly | Ala | Cys | Val | Pro | Arg | Cys | Pro | Gln | |
| | | | | 250 | | | | | 255 | | | | | 260 | | |
| CCT | CTT | GTC | TAC | AAC | AAG | CTA | ACT | TTC | CAG | CTG | GAA | CCC | AAT | CCC | CAC | 930 |
| Pro | Leu | Val | Tyr | Asn | Lys | Leu | Thr | Phe | Gln | Leu | Glu | Pro | Asn | Pro | His | |
| | | | 265 | | | | | 270 | | | | | 275 | | | |
| ACC | AAG | TAT | CAG | TAT | GGA | GGA | GTT | TGT | GTA | GCC | AGC | TGT | CCC | CAT | AAC | 978 |
| Thr | Lys | Tyr | Gln | Tyr | Gly | Gly | Val | Cys | Val | Ala | Ser | Cys | Pro | His | Asn | |
| | | | 280 | | | | | 285 | | | | | 290 | | | |
| TTT | GTG | GTG | GAT | CAA | ACA | TCC | TGT | GTC | AGG | GCC | TGT | CCT | CCT | GAC | AAG | 1026 |
| Phe | Val | Val | Asp | Gln | Thr | Ser | Cys | Val | Arg | Ala | Cys | Pro | Pro | Asp | Lys | |
| | 295 | | | | | 300 | | | | | 305 | | | | | |
| ATG | GAA | GTA | GAT | AAA | AAT | GGG | CTC | AAG | ATG | TGT | GAG | CCT | TGT | GGG | GGA | 1074 |
| Met | Glu | Val | Asp | Lys | Asn | Gly | Leu | Lys | Met | Cys | Glu | Pro | Cys | Gly | Gly | |
| 310 | | | | | 315 | | | | | 320 | | | | | 325 | |
| CTA | TGT | CCC | AAA | GCC | TGT | GAG | GGA | ACA | GGC | TCT | GGG | AGC | CGC | TTC | CAG | 1122 |
| Leu | Cys | Pro | Lys | Ala | Cys | Glu | Gly | Thr | Gly | Ser | Gly | Ser | Arg | Phe | Gln | |
| | | | 330 | | | | | 335 | | | | | 340 | | | |
| ACT | GTG | GAC | TCG | AGC | AAC | ATT | GAT | GGA | TTT | GTG | AAC | TGC | ACC | AAG | ATC | 1170 |
| Thr | Val | Asp | Ser | Ser | Asn | Ile | Asp | Gly | Phe | Val | Asn | Cys | Thr | Lys | Ile | |
| | | | 345 | | | | | 350 | | | | | 355 | | | |
| CTG | GGC | AAC | CTG | GAC | TTT | CTG | ATC | ACC | GGC | CTC | AAT | GGA | GAC | CCC | TGG | 1218 |
| Leu | Gly | Asn | Leu | Asp | Phe | Leu | Ile | Thr | Gly | Leu | Asn | Gly | Asp | Pro | Trp | |
| | | | 360 | | | | | 365 | | | | | 370 | | | |
| CAC | AAG | ATC | CCT | GCC | CTG | GAC | CCA | GAG | AAG | CTC | AAT | GTC | TTC | CGG | ACA | 1266 |
| His | Lys | Ile | Pro | Ala | Leu | Asp | Pro | Glu | Lys | Leu | Asn | Val | Phe | Arg | Thr | |
| | 375 | | | | | 380 | | | | | 385 | | | | | |
| GTA | CGG | GAG | ATC | ACA | GGT | TAC | CTG | AAC | ATC | CAG | TCC | TGG | CCG | CCC | CAC | 1314 |
| Val | Arg | Glu | Ile | Thr | Gly | Tyr | Leu | Asn | Ile | Gln | Ser | Trp | Pro | Pro | His | |
| 390 | | | | | 395 | | | | | 400 | | | | | 405 | |
| ATG | CAC | AAC | TTC | AGT | GTT | TTT | TCC | AAT | TTG | ACA | ACC | ATT | GGA | GGC | AGA | 1362 |
| Met | His | Asn | Phe | Ser | Val | Phe | Ser | Asn | Leu | Thr | Thr | Ile | Gly | Gly | Arg | |
| | | | | 410 | | | | | 415 | | | | | 420 | | |
| AGC | CTC | TAC | AAC | CGG | GGC | TTC | TCA | TTG | TTG | ATC | ATG | AAG | AAC | TTG | AAT | 1410 |
| Ser | Leu | Tyr | Asn | Arg | Gly | Phe | Ser | Leu | Leu | Ile | Met | Lys | Asn | Leu | Asn | |
| | | | 425 | | | | | 430 | | | | | 435 | | | |
| GTC | ACA | TCT | CTG | GGC | TTC | CGA | TCC | CTG | AAG | GAA | ATT | AGT | GCT | GGG | CGT | 1458 |
| Val | Thr | Ser | Leu | Gly | Phe | Arg | Ser | Leu | Lys | Glu | Ile | Ser | Ala | Gly | Arg | |
| | | | 440 | | | | | 445 | | | | | 450 | | | |
| ATC | TAT | ATA | AGT | GCC | AAT | AGG | CAG | CTC | TGC | TAC | CAC | CAC | TCT | TTG | AAC | 1506 |
| Ile | Tyr | Ile | Ser | Ala | Asn | Arg | Gln | Leu | Cys | Tyr | His | His | Ser | Leu | Asn | |
| | | | 455 | | | | | 460 | | | | | 465 | | | |
| TGG | ACC | AAG | GTG | CTT | CGG | GGG | CCT | ACG | GAA | GAG | CGA | CTA | GAC | ATC | AAG | 1554 |
| Trp | Thr | Lys | Val | Leu | Arg | Gly | Pro | Thr | Glu | Glu | Arg | Leu | Asp | Ile | Lys | |
| | 470 | | | | | 475 | | | | | 480 | | | | | 485 |

| | | | | | | | | | | | | | | | | |
|---|---|---|---|---|---|---|---|---|---|---|---|---|---|---|---|---|
| CAT | AAT | CGG | CCG | CGC | AGA | GAC | TGC | GTG | GCA | GAG | GGC | AAA | GTG | TGT | GAC | 1602 |
| His | Asn | Arg | Pro | Arg | Arg | Asp | Cys | Val | Ala | Glu | Gly | Lys | Val | Cys | Asp | |
| | | | 490 | | | | | 495 | | | | | 500 | | | |
| CCA | CTG | TGC | TCC | TCT | GGG | GGA | TGC | TGG | GGC | CCA | GGC | CCT | GGT | CAG | TGC | 1650 |
| Pro | Leu | Cys | Ser | Ser | Gly | Gly | Cys | Trp | Gly | Pro | Gly | Pro | Gly | Gln | Cys | |
| | | | 505 | | | | | 510 | | | | | 515 | | | |
| TTG | TCC | TGT | CGA | AAT | TAT | AGC | CGA | GGA | GGT | GTC | TGT | GTG | ACC | CAC | TGC | 1698 |
| Leu | Ser | Cys | Arg | Asn | Tyr | Ser | Arg | Gly | Gly | Val | Cys | Val | Thr | His | Cys | |
| | | | 520 | | | | | 525 | | | | | 530 | | | |
| AAC | TTT | CTG | AAT | GGG | GAG | CCT | CGA | GAA | TTT | GCC | CAT | GAG | GCC | GAA | TGC | 1746 |
| Asn | Phe | Leu | Asn | Gly | Glu | Pro | Arg | Glu | Phe | Ala | His | Glu | Ala | Glu | Cys | |
| | | | 535 | | | | | 540 | | | | | 545 | | | |
| TTC | TCC | TGC | CAC | CCG | GAA | TGC | CAA | CCC | ATG | GAG | GGC | ACT | GCC | ACA | TGC | 1794 |
| Phe | Ser | Cys | His | Pro | Glu | Cys | Gln | Pro | Met | Glu | Gly | Thr | Ala | Thr | Cys | |
| 550 | | | | | 555 | | | | | 560 | | | | | 565 | |
| AAT | GGC | TCG | GGC | TCT | GAT | ACT | TGT | GCT | CAA | TGT | GCC | CAT | TTT | CGA | GAT | 1842 |
| Asn | Gly | Ser | Gly | Ser | Asp | Thr | Cys | Ala | Gln | Cys | Ala | His | Phe | Arg | Asp | |
| | | | | 570 | | | | | 575 | | | | | 580 | | |
| GGG | CCC | CAC | TGT | GTG | AGC | AGC | TGC | CCC | CAT | GGA | GTC | CTA | GGT | GCC | AAG | 1890 |
| Gly | Pro | His | Cys | Val | Ser | Ser | Cys | Pro | His | Gly | Val | Leu | Gly | Ala | Lys | |
| | | | 585 | | | | | 590 | | | | | 595 | | | |
| GGC | CCA | ATC | TAC | AAG | TAC | CCA | GAT | GTT | CAG | AAT | GAA | TGT | CGG | CCC | TGC | 1938 |
| Gly | Pro | Ile | Tyr | Lys | Tyr | Pro | Asp | Val | Gln | Asn | Glu | Cys | Arg | Pro | Cys | |
| | | 600 | | | | | 605 | | | | | 610 | | | | |
| CAT | GAG | AAC | TGC | ACC | CAG | GGG | TGT | AAA | GGA | CCA | GAG | CTT | CAA | GAC | TGT | 1986 |
| His | Glu | Asn | Cys | Thr | Gln | Gly | Cys | Lys | Gly | Pro | Glu | Leu | Gln | Asp | Cys | |
| | 615 | | | | | 620 | | | | | 625 | | | | | |
| TTA | GGA | CAA | ACA | CTG | GTG | CTG | ATC | GGC | AAA | ACC | CAT | CTG | ACA | ATG | GCT | 2034 |
| Leu | Gly | Gln | Thr | Leu | Val | Leu | Ile | Gly | Lys | Thr | His | Leu | Thr | Met | Ala | |
| 630 | | | | | 635 | | | | | 640 | | | | | 645 | |
| TTG | ACA | GTG | ATA | GCA | GGA | TTG | GTA | GTG | ATT | TTC | ATG | ATG | CTG | GGC | GGC | 2082 |
| Leu | Thr | Val | Ile | Ala | Gly | Leu | Val | Val | Ile | Phe | Met | Met | Leu | Gly | Gly | |
| | | | | 650 | | | | | 655 | | | | | 660 | | |
| ACT | TTT | CTC | TAC | TGG | CGT | GGG | CGC | CGG | ATT | CAG | AAT | AAA | AGG | GCT | ATG | 2130 |
| Thr | Phe | Leu | Tyr | Trp | Arg | Gly | Arg | Arg | Ile | Gln | Asn | Lys | Arg | Ala | Met | |
| | | | 665 | | | | | 670 | | | | | 675 | | | |
| AGG | CGA | TAC | TTG | GAA | CGG | GGT | GAG | AGC | ATA | GAG | CCT | CTG | GAC | CCC | AGT | 2178 |
| Arg | Arg | Tyr | Leu | Glu | Arg | Gly | Glu | Ser | Ile | Glu | Pro | Leu | Asp | Pro | Ser | |
| | | 680 | | | | | 685 | | | | | 690 | | | | |
| GAG | AAG | GCT | AAC | AAA | GTC | TTG | GCC | AGA | ATC | TTC | AAA | GAG | ACA | GAG | CTA | 2226 |
| Glu | Lys | Ala | Asn | Lys | Val | Leu | Ala | Arg | Ile | Phe | Lys | Glu | Thr | Glu | Leu | |
| | 695 | | | | | 700 | | | | | 705 | | | | | |
| AGG | AAG | CTT | AAA | GTG | CTT | GGC | TCG | GGT | GTC | TTT | GGA | ACT | GTG | CAC | AAA | 2274 |
| Arg | Lys | Leu | Lys | Val | Leu | Gly | Ser | Gly | Val | Phe | Gly | Thr | Val | His | Lys | |
| 710 | | | | | 715 | | | | | 720 | | | | | 725 | |
| GGA | GTG | TGG | ATC | CCT | GAG | GGT | GAA | TCA | ATC | AAG | ATT | CCA | GTC | TGC | ATT | 2322 |
| Gly | Val | Trp | Ile | Pro | Glu | Gly | Glu | Ser | Ile | Lys | Ile | Pro | Val | Cys | Ile | |
| | | | | 730 | | | | | 735 | | | | | 740 | | |
| AAA | GTC | ATT | GAG | GAC | AAG | AGT | GGA | CGG | CAG | AGT | TTT | CAA | GCT | GTG | ACA | 2370 |
| Lys | Val | Ile | Glu | Asp | Lys | Ser | Gly | Arg | Gln | Ser | Phe | Gln | Ala | Val | Thr | |
| | | | 745 | | | | | 750 | | | | | 755 | | | |
| GAT | CAT | ATG | CTG | GCC | ATT | GGC | AGC | CTG | GAC | CAT | GCC | CAC | ATT | GTA | AGG | 2418 |
| Asp | His | Met | Leu | Ala | Ile | Gly | Ser | Leu | Asp | His | Ala | His | Ile | Val | Arg | |
| | | 760 | | | | | 765 | | | | | 770 | | | | |
| CTG | CTG | GGA | CTA | TGC | CCA | GGG | TCA | TCT | CTG | CAG | CTT | GTC | ACT | CAA | TAT | 2466 |
| Leu | Leu | Gly | Leu | Cys | Pro | Gly | Ser | Ser | Leu | Gln | Leu | Val | Thr | Gln | Tyr | |
| | 775 | | | | | 780 | | | | | 785 | | | | | |
| TTG | CCT | CTG | GGT | TCT | CTG | CTG | GAT | CAT | GTG | AGA | CAA | CAC | CGG | GGG | GCA | 2514 |
| Leu | Pro | Leu | Gly | Ser | Leu | Leu | Asp | His | Val | Arg | Gln | His | Arg | Gly | Ala | |
| 790 | | | | | 795 | | | | | 800 | | | | | 805 | |

```
CTG  GGG  CCA  CAG  CTG  CTG  CTC  AAC  TGG  GGA  GTA  CAA  ATT  GCC  AAG  GGA     2562
Leu  Gly  Pro  Gln  Leu  Leu  Leu  Asn  Trp  Gly  Val  Gln  Ile  Ala  Lys  Gly
                    810                      815                      820

ATG  TAC  TAC  CTT  GAG  GAA  CAT  GGT  ATG  GTG  CAT  AGA  AAC  CTG  GCT  GCC     2610
Met  Tyr  Tyr  Leu  Glu  Glu  His  Gly  Met  Val  His  Arg  Asn  Leu  Ala  Ala
               825                      830                      835

CGA  AAC  GTG  CTA  CTC  AAG  TCA  CCC  AGT  CAG  GTT  CAG  GTG  GCA  GAT  TTT     2658
Arg  Asn  Val  Leu  Leu  Lys  Ser  Pro  Ser  Gln  Val  Gln  Val  Ala  Asp  Phe
          840                      845                      850

GGT  GTG  GCT  GAC  CTG  CTG  CCT  CCT  GAT  GAT  AAG  CAG  CTG  CTA  TAC  AGT     2706
Gly  Val  Ala  Asp  Leu  Leu  Pro  Pro  Asp  Asp  Lys  Gln  Leu  Leu  Tyr  Ser
     855                      860                      865

GAG  GCC  AAG  ACT  CCA  ATT  AAG  TGG  ATG  GCC  CTT  GAG  AGT  ATC  CAC  TTT     2754
Glu  Ala  Lys  Thr  Pro  Ile  Lys  Trp  Met  Ala  Leu  Glu  Ser  Ile  His  Phe
870                      875                      880                      885

GGG  AAA  TAC  ACA  CAC  CAG  AGT  GAT  GTC  TGG  AGC  TAT  GGT  GTG  ACA  GTT     2802
Gly  Lys  Tyr  Thr  His  Gln  Ser  Asp  Val  Trp  Ser  Tyr  Gly  Val  Thr  Val
                    890                      895                      900

TGG  GAG  TTG  ATG  ACC  TTC  GGG  GCA  GAG  CCC  TAT  GCA  GGG  CTA  CGA  TTG     2850
Trp  Glu  Leu  Met  Thr  Phe  Gly  Ala  Glu  Pro  Tyr  Ala  Gly  Leu  Arg  Leu
               905                      910                      915

GCT  GAA  GTA  CCA  GAC  CTG  CTA  GAG  AAG  GGG  GAG  CGG  TTG  GCA  CAG  CCC     2898
Ala  Glu  Val  Pro  Asp  Leu  Leu  Glu  Lys  Gly  Glu  Arg  Leu  Ala  Gln  Pro
          920                      925                      930

CAG  ATC  TGC  ACA  ATT  GAT  GTC  TAC  ATG  GTG  ATG  GTC  AAG  TGT  TGG  ATG     2946
Gln  Ile  Cys  Thr  Ile  Asp  Val  Tyr  Met  Val  Met  Val  Lys  Cys  Trp  Met
     935                      940                      945

ATT  GAT  GAG  AAC  ATT  CGC  CCA  ACC  TTT  AAA  GAA  CTA  GCC  AAT  GAG  TTC     2994
Ile  Asp  Glu  Asn  Ile  Arg  Pro  Thr  Phe  Lys  Glu  Leu  Ala  Asn  Glu  Phe
950                      955                      960                      965

ACC  AGG  ATG  GCC  CGA  GAC  CCA  CCA  CGG  TAT  CTG  GTC  ATA  AAG  AGA  GAG     3042
Thr  Arg  Met  Ala  Arg  Asp  Pro  Pro  Arg  Tyr  Leu  Val  Ile  Lys  Arg  Glu
                    970                      975                      980

AGT  GGG  CCT  GGA  ATA  GCC  CCT  GGG  CCA  GAG  CCC  CAT  GGT  CTG  ACA  AAC     3090
Ser  Gly  Pro  Gly  Ile  Ala  Pro  Gly  Pro  Glu  Pro  His  Gly  Leu  Thr  Asn
               985                      990                      995

AAG  AAG  CTA  GAG  GAA  GTA  GAG  CTG  GAG  CCA  GAA  CTA  GAC  CTA  GAC  CTA     3138
Lys  Lys  Leu  Glu  Glu  Val  Glu  Leu  Glu  Pro  Glu  Leu  Asp  Leu  Asp  Leu
          1000                     1005                     1010

GAC  TTG  GAA  GCA  GAG  GAG  GAC  AAC  CTG  GCA  ACC  ACC  ACA  CTG  GGC  TCC     3186
Asp  Leu  Glu  Ala  Glu  Glu  Asp  Asn  Leu  Ala  Thr  Thr  Thr  Leu  Gly  Ser
     1015                     1020                     1025

GCC  CTC  AGC  CTA  CCA  GTT  GGA  ACA  CTT  AAT  CGG  CCA  CGT  GGG  AGC  CAG     3234
Ala  Leu  Ser  Leu  Pro  Val  Gly  Thr  Leu  Asn  Arg  Pro  Arg  Gly  Ser  Gln
1030                     1035                     1040                     1045

AGC  CTT  TTA  AGT  CCA  TCA  TCT  GGA  TAC  ATG  CCC  ATG  AAC  CAG  GGT  AAT     3282
Ser  Leu  Leu  Ser  Pro  Ser  Ser  Gly  Tyr  Met  Pro  Met  Asn  Gln  Gly  Asn
               1050                     1055                     1060

CTT  GGG  GAG  TCT  TGC  CAG  GAG  TCT  GCA  GTT  TCT  GGG  AGC  AGT  GAA  CGG     3330
Leu  Gly  Glu  Ser  Cys  Gln  Glu  Ser  Ala  Val  Ser  Gly  Ser  Ser  Glu  Arg
                    1065                     1070                     1075

TGC  CCC  CGT  CCA  GTC  TCT  CTA  CAC  CCA  ATG  CCA  CGG  GGA  TGC  CTG  GCA     3378
Cys  Pro  Arg  Pro  Val  Ser  Leu  His  Pro  Met  Pro  Arg  Gly  Cys  Leu  Ala
               1080                     1085                     1090

TCA  GAG  TCA  TCA  GAG  GGG  CAT  GTA  ACA  GGC  TCT  GAG  GCT  GAG  CTC  CAG     3426
Ser  Glu  Ser  Ser  Glu  Gly  His  Val  Thr  Gly  Ser  Glu  Ala  Glu  Leu  Gln
     1095                     1100                     1105

GAG  AAA  GTG  TCA  ATG  TGT  AGA  AGC  CGG  AGC  AGG  AGC  CGG  AGC  CCA  CGG     3474
Glu  Lys  Val  Ser  Met  Cys  Arg  Ser  Arg  Ser  Arg  Ser  Arg  Ser  Pro  Arg
1110                     1115                     1120                     1125
```

```
CCA  CGC  GGA  GAT  AGC  GCC  TAC  CAT  TCC  CAG  CGC  CAC  AGT  CTG  CTG  ACT      3522
Pro  Arg  Gly  Asp  Ser  Ala  Tyr  His  Ser  Gln  Arg  His  Ser  Leu  Leu  Thr
               1130                    1135                    1140

CCT  GTT  ACC  CCA  CTC  TCC  CCA  CCC  GGG  TTA  GAG  GAA  GAG  GAT  GTC  AAC      3570
Pro  Val  Thr  Pro  Leu  Ser  Pro  Pro  Gly  Leu  Glu  Glu  Glu  Asp  Val  Asn
               1145                    1150                    1155

GGT  TAT  GTC  ATG  CCA  GAT  ACA  CAC  CTC  AAA  GGT  ACT  CCC  TCC  TCC  CGG      3618
Gly  Tyr  Val  Met  Pro  Asp  Thr  His  Leu  Lys  Gly  Thr  Pro  Ser  Ser  Arg
               1160                    1165                    1170

GAA  GGC  ACC  CTT  TCT  TCA  GTG  GGT  CTT  AGT  TCT  GTC  CTG  GGT  ACT  GAA      3666
Glu  Gly  Thr  Leu  Ser  Ser  Val  Gly  Leu  Ser  Ser  Val  Leu  Gly  Thr  Glu
               1175                    1180                    1185

GAA  GAA  GAT  GAA  GAT  GAG  GAG  TAT  GAA  TAC  ATG  AAC  CGG  AGG  AGA  AGG      3714
Glu  Glu  Asp  Glu  Asp  Glu  Glu  Tyr  Glu  Tyr  Met  Asn  Arg  Arg  Arg  Arg
1190                     1195                    1200                    1205

CAC  AGT  CCA  CCT  CAT  CCC  CCT  AGG  CCA  AGT  TCC  CTT  GAG  GAG  CTG  GGT      3762
His  Ser  Pro  Pro  His  Pro  Pro  Arg  Pro  Ser  Ser  Leu  Glu  Glu  Leu  Gly
               1210                    1215                    1220

TAT  GAG  TAC  ATG  GAT  GTG  GGG  TCA  GAC  CTC  AGT  GCC  TCT  CTG  GGC  AGC      3810
Tyr  Glu  Tyr  Met  Asp  Val  Gly  Ser  Asp  Leu  Ser  Ala  Ser  Leu  Gly  Ser
               1225                    1230                    1235

ACA  CAG  AGT  TGC  CCA  CTC  CAC  CCT  GTA  CCC  ATC  ATG  CCC  ACT  GCA  GGC      3858
Thr  Gln  Ser  Cys  Pro  Leu  His  Pro  Val  Pro  Ile  Met  Pro  Thr  Ala  Gly
               1240                    1245                    1250

ACA  ACT  CCA  GAT  GAA  GAC  TAT  GAA  TAT  ATG  AAT  CGG  CAA  CGA  GAT  GGA      3906
Thr  Thr  Pro  Asp  Glu  Asp  Tyr  Glu  Tyr  Met  Asn  Arg  Gln  Arg  Asp  Gly
               1255                    1260                    1265

GGT  GGT  CCT  GGG  GGT  GAT  TAT  GCA  GCC  ATG  GGG  GCC  TGC  CCA  GCA  TCT      3954
Gly  Gly  Pro  Gly  Gly  Asp  Tyr  Ala  Ala  Met  Gly  Ala  Cys  Pro  Ala  Ser
1270                     1275                    1280                    1285

GAG  CAA  GGG  TAT  GAA  GAG  ATG  AGA  GCT  TTT  CAG  GGG  CCT  GGA  CAT  CAG      4002
Glu  Gln  Gly  Tyr  Glu  Glu  Met  Arg  Ala  Phe  Gln  Gly  Pro  Gly  His  Gln
               1290                    1295                    1300

GCC  CCC  CAT  GTC  CAT  TAT  GCC  CGC  CTA  AAA  ACT  CTA  CGT  AGC  TTA  GAG      4050
Ala  Pro  His  Val  His  Tyr  Ala  Arg  Leu  Lys  Thr  Leu  Arg  Ser  Leu  Glu
               1305                    1310                    1315

GCT  ACA  GAC  TCT  GCC  TTT  GAT  AAC  CCT  GAT  TAC  TGG  CAT  AGC  AGG  CTT      4098
Ala  Thr  Asp  Ser  Ala  Phe  Asp  Asn  Pro  Asp  Tyr  Trp  His  Ser  Arg  Leu
               1320                    1325                    1330

TTC  CCC  AAG  GCT  AAT  GCC  CAG  AGA  ACG  TAACTCCTGC  TCCCTGTGGC                  4145
Phe  Pro  Lys  Ala  Asn  Ala  Gln  Arg  Thr
               1335                    1340

ACTCAGGGAG  CATTTAATGG  CAGCTAGTGC  CTTTAGAGGG  TACCGTCTTC  TCCCTATTCC              4205

CTCTCTCTCC  CAGGTCCCAG  CCCCTTTTCC  CCAGTCCCAG  ACAATTCCAT  TCAATCTTTG              4265

GAGGCTTTTA  AACATTTTGA  CACAAAATTC  TTATGGTATG  TAGCCAGCTG  TGCACTTTCT              4325

TCTCTTTCCC  AACCCCAGGA  AAGGTTTTCC  TTATTTTGTG  TGCTTTCCCA  GTCCCATTCC              4385

TCAGCTTCTT  CACAGGCACT  CCTGGAGATA  TGAAGGATTA  CTCTCCATAT  CCCTTCCTCT              4445

CAGGCTCTTG  ACTACTTGGA  ACTAGGCTCT  TATGTGTGCC  TTTGTTTCCC  ATCAGACTGT              4505

CAAGAAGAGG  AAAGGGAGGA  AACCTAGCAG  AGGAAAGTGT  AATTTTGGTT  TATGACTCTT              4565

AACCCCCTAG  AAAGACAGAA  GCTTAAAATC  TGTGAAGAAA  GAGGTTAGGA  GTAGATATTG              4625

ATTACTATCA  TAATTCAGCA  CTTAACTATG  AGCCAGGCAT  CATACTAAAC  TTCACCTACA              4685

TTATCTCACT  TAGTCCTTTA  TCATCCTTAA  AACAATTCTG  TGACATACAT  ATTATCTCAT              4745

TTTACACAAA  GGGAAGTCGG  GCATGGTGGC  TCATGCCTGT  AATCTCAGCA  CTTTGGGAGG              4805

CTGAGGCAGA  AGGATTACCT  GAGGCAAGGA  GTTTGAGACC  AGCTTAGCCA  ACATAGTAAG              4865
```

ACCCCCATCT CTTTAAAAAA AAAAAAAAAA AAAAAAAAA                    4905

(2) INFORMATION FOR SEQ ID NO:4:

(i) SEQUENCE CHARACTERISTICS:
        (A) LENGTH: 1342 amino acids
        (B) TYPE: amino acid
        (D) TOPOLOGY: linear (ii) MOLECULE TYPE: protein (xi) SEQUENCE DESCRIPTION: SEQ ID NO:4:

```
Met  Arg  Ala  Asn  Asp  Ala  Leu  Gln  Val  Leu  Gly  Leu  Leu  Phe  Ser  Leu
  1             5                      10                      15
Ala  Arg  Gly  Ser  Glu  Val  Gly  Asn  Ser  Gln  Ala  Val  Cys  Pro  Gly  Thr
                20                      25                      30
Leu  Asn  Gly  Leu  Ser  Val  Thr  Gly  Asp  Ala  Glu  Asn  Gln  Tyr  Gln  Thr
            35                      40                      45
Leu  Tyr  Lys  Leu  Tyr  Glu  Arg  Cys  Glu  Val  Val  Met  Gly  Asn  Leu  Glu
        50                      55                      60
Ile  Val  Leu  Thr  Gly  His  Asn  Ala  Asp  Leu  Ser  Phe  Leu  Gln  Trp  Ile
 65                      70                      75                      80
Arg  Glu  Val  Thr  Gly  Tyr  Val  Leu  Val  Ala  Met  Asn  Glu  Phe  Ser  Thr
                    85                      90                      95
Leu  Pro  Leu  Pro  Asn  Leu  Arg  Val  Val  Arg  Gly  Thr  Gln  Val  Tyr  Asp
                100                     105                     110
Gly  Lys  Phe  Ala  Ile  Phe  Val  Met  Leu  Asn  Tyr  Asn  Thr  Asn  Ser  Ser
            115                     120                     125
His  Ala  Leu  Arg  Gln  Leu  Arg  Leu  Thr  Gln  Leu  Thr  Glu  Ile  Leu  Ser
        130                     135                     140
Gly  Gly  Val  Tyr  Ile  Glu  Lys  Asn  Asp  Lys  Leu  Cys  His  Met  Asp  Thr
145                     150                     155                     160
Ile  Asp  Trp  Arg  Asp  Ile  Val  Arg  Asp  Arg  Asp  Ala  Glu  Ile  Val  Val
                    165                     170                     175
Lys  Asp  Asn  Gly  Arg  Ser  Cys  Pro  Pro  Cys  His  Glu  Val  Cys  Lys  Gly
                180                     185                     190
Arg  Cys  Trp  Gly  Pro  Gly  Ser  Glu  Asp  Cys  Gln  Thr  Leu  Thr  Lys  Thr
            195                     200                     205
Ile  Cys  Ala  Pro  Gln  Cys  Asn  Gly  His  Cys  Phe  Gly  Pro  Asn  Pro  Asn
        210                     215                     220
Gln  Cys  Cys  His  Asp  Glu  Cys  Ala  Gly  Gly  Cys  Ser  Gly  Pro  Gln  Asp
225                     230                     235                     240
Thr  Asp  Cys  Phe  Ala  Cys  Arg  His  Phe  Asn  Asp  Ser  Gly  Ala  Cys  Val
                    245                     250                     255
Pro  Arg  Cys  Pro  Gln  Pro  Leu  Val  Tyr  Asn  Lys  Leu  Thr  Phe  Gln  Leu
                260                     265                     270
Glu  Pro  Asn  Pro  His  Thr  Lys  Tyr  Gln  Tyr  Gly  Gly  Val  Cys  Val  Ala
            275                     280                     285
Ser  Cys  Pro  His  Asn  Phe  Val  Val  Asp  Gln  Thr  Ser  Cys  Val  Arg  Ala
        290                     295                     300
Cys  Pro  Pro  Asp  Lys  Met  Glu  Val  Asp  Lys  Asn  Gly  Leu  Lys  Met  Cys
305                     310                     315                     320
Glu  Pro  Cys  Gly  Gly  Leu  Cys  Pro  Lys  Ala  Cys  Glu  Gly  Thr  Gly  Ser
                    325                     330                     335
Gly  Ser  Arg  Phe  Gln  Thr  Val  Asp  Ser  Ser  Asn  Ile  Asp  Gly  Phe  Val
                340                     345                     350
```

```
Asn Cys Thr Lys Ile Leu Gly Asn Leu Asp Phe Leu Ile Thr Gly Leu
        355                 360                 365
Asn Gly Asp Pro Trp His Lys Ile Pro Ala Leu Asp Pro Glu Lys Leu
    370                 375                 380
Asn Val Phe Arg Thr Val Arg Glu Ile Thr Gly Tyr Leu Asn Ile Gln
385                 390                 395                 400
Ser Trp Pro Pro His Met His Asn Phe Ser Val Phe Ser Asn Leu Thr
                405                 410                 415
Thr Ile Gly Gly Arg Ser Leu Tyr Asn Arg Gly Phe Ser Leu Leu Ile
                420                 425                 430
Met Lys Asn Leu Asn Val Thr Ser Leu Gly Phe Arg Ser Leu Lys Glu
        435                 440                 445
Ile Ser Ala Gly Arg Ile Tyr Ile Ser Ala Asn Arg Gln Leu Cys Tyr
    450                 455                 460
His His Ser Leu Asn Trp Thr Lys Val Leu Arg Gly Pro Thr Glu Glu
465                 470                 475                 480
Arg Leu Asp Ile Lys His Asn Arg Pro Arg Arg Asp Cys Val Ala Glu
                485                 490                 495
Gly Lys Val Cys Asp Pro Leu Cys Ser Gly Gly Cys Trp Gly Pro
                500                 505                 510
Gly Pro Gly Gln Cys Leu Ser Cys Arg Asn Tyr Ser Arg Gly Gly Val
        515                 520                 525
Cys Val Thr His Cys Asn Phe Leu Asn Gly Glu Pro Arg Glu Phe Ala
    530                 535                 540
His Glu Ala Glu Cys Phe Ser Cys His Pro Glu Cys Gln Pro Met Glu
545                 550                 555                 560
Gly Thr Ala Thr Cys Asn Gly Ser Gly Ser Asp Thr Cys Ala Gln Cys
                565                 570                 575
Ala His Phe Arg Asp Gly Pro His Cys Val Ser Cys Pro His Gly
        580                 585                 590
Val Leu Gly Ala Lys Gly Pro Ile Tyr Lys Tyr Pro Asp Val Gln Asn
    595                 600                 605
Glu Cys Arg Pro Cys His Glu Asn Cys Thr Gln Gly Cys Lys Gly Pro
610                 615                 620
Glu Leu Gln Asp Cys Leu Gly Gln Thr Leu Val Leu Ile Gly Lys Thr
625                 630                 635                 640
His Leu Thr Met Ala Leu Thr Val Ile Ala Gly Leu Val Val Ile Phe
                645                 650                 655
Met Met Leu Gly Gly Thr Phe Leu Tyr Trp Arg Gly Arg Arg Ile Gln
            660                 665                 670
Asn Lys Arg Ala Met Arg Arg Tyr Leu Glu Arg Gly Glu Ser Ile Glu
        675                 680                 685
Pro Leu Asp Pro Ser Glu Lys Ala Asn Lys Val Leu Ala Arg Ile Phe
    690                 695                 700
Lys Glu Thr Glu Leu Arg Lys Leu Lys Val Leu Gly Ser Gly Val Phe
705                 710                 715                 720
Gly Thr Val His Lys Gly Val Trp Ile Pro Glu Gly Glu Ser Ile Lys
                725                 730                 735
Ile Pro Val Cys Ile Lys Val Ile Glu Asp Lys Ser Gly Arg Gln Ser
            740                 745                 750
Phe Gln Ala Val Thr Asp His Met Leu Ala Ile Gly Ser Leu Asp His
        755                 760                 765
Ala His Ile Val Arg Leu Leu Gly Leu Cys Pro Gly Ser Ser Leu Gln
```

-continued

```
            770                     775                     780
Leu  Val  Thr  Gln  Tyr  Leu  Pro  Leu  Gly  Ser  Leu  Leu  Asp  His  Val  Arg
785                      790                     795                     800

Gln  His  Arg  Gly  Ala  Leu  Gly  Pro  Gln  Leu  Leu  Leu  Asn  Trp  Gly  Val
                    805                     810                     815

Gln  Ile  Ala  Lys  Gly  Met  Tyr  Tyr  Leu  Glu  Glu  His  Gly  Met  Val  His
                    820                     825                     830

Arg  Asn  Leu  Ala  Ala  Arg  Asn  Val  Leu  Leu  Lys  Ser  Pro  Ser  Gln  Val
               835                     840                     845

Gln  Val  Ala  Asp  Phe  Gly  Val  Ala  Asp  Leu  Leu  Pro  Pro  Asp  Asp  Lys
               850                     855                     860

Gln  Leu  Leu  Tyr  Ser  Glu  Ala  Lys  Thr  Pro  Ile  Lys  Trp  Met  Ala  Leu
865                      870                     875                     880

Glu  Ser  Ile  His  Phe  Gly  Lys  Tyr  Thr  His  Gln  Ser  Asp  Val  Trp  Ser
                    885                     890                     895

Tyr  Gly  Val  Thr  Val  Trp  Glu  Leu  Met  Thr  Phe  Gly  Ala  Glu  Pro  Tyr
                    900                     905                     910

Ala  Gly  Leu  Arg  Leu  Ala  Glu  Val  Pro  Asp  Leu  Leu  Glu  Lys  Gly  Glu
                    915                     920                     925

Arg  Leu  Ala  Gln  Pro  Gln  Ile  Cys  Thr  Ile  Asp  Val  Tyr  Met  Val  Met
930                      935                     940

Val  Lys  Cys  Trp  Met  Ile  Asp  Glu  Asn  Ile  Arg  Pro  Thr  Phe  Lys  Glu
945                      950                     955                     960

Leu  Ala  Asn  Glu  Phe  Thr  Arg  Met  Ala  Arg  Asp  Pro  Pro  Arg  Tyr  Leu
                    965                     970                     975

Val  Ile  Lys  Arg  Glu  Ser  Gly  Pro  Gly  Ile  Ala  Pro  Gly  Pro  Glu  Pro
                    980                     985                     990

His  Gly  Leu  Thr  Asn  Lys  Lys  Leu  Glu  Glu  Val  Glu  Leu  Glu  Pro  Glu
                    995                     1000                    1005

Leu  Asp  Leu  Asp  Leu  Asp  Leu  Glu  Ala  Glu  Glu  Asp  Asn  Leu  Ala  Thr
                    1010                    1015                    1020

Thr  Thr  Leu  Gly  Ser  Ala  Leu  Ser  Leu  Pro  Val  Gly  Thr  Leu  Asn  Arg
1025                     1030                    1035                    1040

Pro  Arg  Gly  Ser  Gln  Ser  Leu  Leu  Ser  Pro  Ser  Ser  Gly  Tyr  Met  Pro
                    1045                    1050                    1055

Met  Asn  Gln  Gly  Asn  Leu  Gly  Glu  Ser  Cys  Gln  Glu  Ser  Ala  Val  Ser
                    1060                    1065                    1070

Gly  Ser  Ser  Glu  Arg  Cys  Pro  Arg  Pro  Val  Ser  Leu  His  Pro  Met  Pro
                    1075                    1080                    1085

Arg  Gly  Cys  Leu  Ala  Ser  Glu  Ser  Ser  Glu  Gly  His  Val  Thr  Gly  Ser
                    1090                    1095                    1100

Glu  Ala  Glu  Leu  Gln  Glu  Lys  Val  Ser  Met  Cys  Arg  Ser  Arg  Ser  Arg
1105                     1110                    1115                    1120

Ser  Arg  Ser  Pro  Arg  Pro  Arg  Gly  Asp  Ser  Ala  Tyr  His  Ser  Gln  Arg
                    1125                    1130                    1135

His  Ser  Leu  Leu  Thr  Pro  Val  Thr  Pro  Leu  Ser  Pro  Pro  Gly  Leu  Glu
                    1140                    1145                    1150

Glu  Glu  Asp  Val  Asn  Gly  Tyr  Val  Met  Pro  Asp  Thr  His  Leu  Lys  Gly
                    1155                    1160                    1165

Thr  Pro  Ser  Ser  Arg  Glu  Gly  Thr  Leu  Ser  Ser  Val  Gly  Leu  Ser  Ser
                    1170                    1175                    1180

Val  Leu  Gly  Thr  Glu  Glu  Glu  Asp  Glu  Asp  Glu  Glu  Tyr  Glu  Tyr  Met
1185                     1190                    1195                    1200
```

-continued

Asn Arg Arg Arg Arg His Ser Pro Pro His Pro Pro Arg Pro Ser Ser
              1205                1210              1215

Leu Glu Glu Leu Gly Tyr Glu Tyr Met Asp Val Gly Ser Asp Leu Ser
          1220            1225              1230

Ala Ser Leu Gly Ser Thr Gln Ser Cys Pro Leu His Pro Val Pro Ile
      1235              1240              1245

Met Pro Thr Ala Gly Thr Thr Pro Asp Glu Asp Tyr Glu Tyr Met Asn
  1250              1255              1260

Arg Gln Arg Asp Gly Gly Gly Pro Gly Gly Asp Tyr Ala Ala Met Gly
1265              1270              1275                  1280

Ala Cys Pro Ala Ser Glu Gln Gly Tyr Glu Glu Met Arg Ala Phe Gln
              1285              1290              1295

Gly Pro Gly His Gln Ala Pro His Val His Tyr Ala Arg Leu Lys Thr
          1300              1305              1310

Leu Arg Ser Leu Glu Ala Thr Asp Ser Ala Phe Asp Asn Pro Asp Tyr
          1315              1320              1325

Trp His Ser Arg Leu Phe Pro Lys Ala Asn Ala Gln Arg Thr
          1330              1335              1340

( 2 ) INFORMATION FOR SEQ ID NO:5:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:5:

Glu Asp Glu Asp Glu Glu Tyr Glu Tyr Met Asn Arg Arg Arg Arg
1           5               10              15

( 2 ) INFORMATION FOR SEQ ID NO:6:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:6:

Thr Thr Pro Asp Glu Asp Tyr Glu Tyr Met Asn Arg Gln Arg Asp
1           5               10              15

( 2 ) INFORMATION FOR SEQ ID NO:7:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:7:

Thr Glu Glu Arg Leu Asp Ile Lys His Asn Arg Pro Arg Arg Asp
1           5               10              15

( 2 ) INFORMATION FOR SEQ ID NO:8:

( i ) SEQUENCE CHARACTERISTICS:
( A ) LENGTH: 15 amino acids
( B ) TYPE: amino acid
( D ) TOPOLOGY: linear ( i i ) MOLECULE TYPE: peptide ( v ) FRAGMENT TYPE: internal ( x i ) SEQUENCE DESCRIPTION: SEQ ID NO:8:

```
Arg Ser Arg Ser Arg Ser Arg Ser Pro Arg Pro Arg Gly Asp Ser
 1               5                  10                  15
```

( 2 ) INFORMATION FOR SEQ ID NO:9:

( i ) SEQUENCE CHARACTERISTICS:
( A ) LENGTH: 15 amino acids
( B ) TYPE: amino acid
( D ) TOPOLOGY: linear ( i i ) MOLECULE TYPE: peptide ( v ) FRAGMENT TYPE: internal ( x i ) SEQUENCE DESCRIPTION: SEQ ID NO:9:

```
Tyr Met Asn Arg Arg Arg Arg His Ser Pro Pro His Pro Pro Arg
 1               5                  10                  15
```

( 2 ) INFORMATION FOR SEQ ID NO:10:

( i ) SEQUENCE CHARACTERISTICS:
( A ) LENGTH: 14 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:10:

GATCTCGAGT CGAC                                                         14

( 2 ) INFORMATION FOR SEQ ID NO:11:

( i ) SEQUENCE CHARACTERISTICS:
( A ) LENGTH: 14 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:11:

GATCGTCGAC TCGA                                                         14

( 2 ) INFORMATION FOR SEQ ID NO:12:

( i ) SEQUENCE CHARACTERISTICS:
( A ) LENGTH: 5 amino acids
( B ) TYPE: amino acid
( D ) TOPOLOGY: linear ( i i ) MOLECULE TYPE: peptide ( v ) FRAGMENT TYPE: internal ( x i ) SEQUENCE DESCRIPTION: SEQ ID NO:12:

```
Tyr Glu Tyr Met Asn
 1               5
```

METHOD OF TARGETING A THERAPEUTIC AGENT TO CELLS EXPRESSING THE ERB B-3 RECEPTOR

This application is a Divisional application of Ser. No. 07/978,895, filed Nov. 10, 1992, now U.S. Pat. No. 5,480,968 issued Jan. 2, 1996 which is a continuation-in-part of Ser. No. 07/444,406, filed Dec. 1, 1989, now U.S. Pat. No. 5,183,884 issued Feb. 2, 1993.

FIELD OF THE INVENTION

The present invention relates to genes which encode novel proteins related to a family of receptor proteins typified by two related membrane spanning tyrosine kinases: the Epidermal Growth Factor receptor (EGFR), which is encoded by the erbB gene, the normal human counterpart of an oncogene (v-erbB) that was first recognized in the proviral DNA of avian crythroblastosis virus; and the receptor encoded by the related gene erbB-2. In particular, the present invention relates to a DNA segment encoding the coding sequence, or a unique portion thereof, for a third member of this receptor gene family, herein designated erbB-3.

BACKGROUND OF THE INVENTION

Proto-oncogenes encoding growth factor receptors constitute several distinct families with close overall structural homology. The highest degree of homology is observed in their catalytic domains, essential for the intrinsic tyrosine kinase activity of these proteins. Examples of such receptor families include: the EGFR and the related product of the erbB-2 oncogene; the Colony Stimulating Factor 1 receptor (CSF-1-R) and the related Platelet-Derived Growth Factor receptor (PDGF-R); the insulin receptor (IR) and the related Insulin-like Growth factor 1 receptor (IGF-1R); and the receptors encoded by the related oncogenes eph and elk.

It is well established that growth factor receptors in several of these families play critical roles in regulation of normal growth and development. Recent studies in Drosophila have emphasized how critical and multifunctional are developmental processes mediated by ligand-receptor interactions. An increasing number of Drosophila mutants with often varying phenotypes have now been identified as being due to lesions in genes encoding such proteins. The genetic locus of the Drosophila EGFR homologue, designated DER, has recently been identified as being allelic to the zygotic embryonic lethal faint little ball exhibiting a complex phenotype with deterioration of multiple tissue components of cctodermal origin. Furthermore, other mutants appear to lack DER function either in the egg or the surrounding maternal tissue. Thus, the DER receptor may play an important role in the ligand-receptor interaction between egg and follicle cells necessary for determination of correct shape of eggshell and embryo. It is not yet known whether DER represents the sole Drosophila counterpart of known mammaliain erbB-related genes.

Some of these receptor molecules have been implicated in the neoplastic process as well. In particular, both the erbB and erbB-2 genes have been shown to be activated as oncogenes by mechanisms involving overexpression or mutations that constitutively activate the catalytic activity, of their encoded receptor proteins (Bargmann, C. I., Hung, M. C. & Weinberg, R. A., 1986, *Cell* 45:649–657; Di Fiore, P. P., Pierce, J. H., Kraus, M. H., Segatto. O., King, C. R. & Aaronson, S. A., 1987, *Science* 237:178–182; Di Fiore, P. P., Pierce, J. H., Fleming, T. P., Hazan, R., Ullrich, A., King, C. R., Schlessinger, J. & Aaronson, S. A., 1987, *Cell* 51:1063–1070; Velu, T. J., Beguinot, L., Vass, W. C., Willingham, M. C., Merlino, G. T., Pastan, I. & Lowy, D.R., 1987, *Science* 238:1408–1410). Both erbB and erbB-2 have been causally implicated in human malignancy. erbB gene amplification or overexpression, or a combination of both, has been demonstrated in squamous cell carcinomas and glioblastomas (Libermann, T. A., Nusbaum, H. R., Razon, N., Kris, R., Lax, I., Soreq, H., Whittie, N., Waterfild, M. D., Ullrich, A. & Schlessinger, J., 1985, *Nature* 313:144–147). erbB-2 amplification and overexpression have been observed in human breast and ovarian carcinomas (King, C. R., Kraus, M. H. & Aaronson S. A., 1985, *Science* 229:974–976; Slamon, D. J., Godolphin, W., Jones, L. A., Holt, J. A., Wong, S. G., Keith, D. E., Levin, W. J., Stuart, S. G., Udove, J., Ullrich, A. & Press, M. F., 1989, *Science* 244:707–712), and erbB-2 overexpression has been reported to be an important prognostic indicator of particularly aggressive tumors (Slamon, D. J., et al., 1989, supra). Yet, not all such tumors have been found to overexpress erbB-2, and many human tumors have not yet been associated with any known oncogene. Thus, there has been a continuing need to search for additional oncogenes which would provide knowledge and methods for diagnosis and, ultimately, for rational molecular therapy of human cancers.

Throughout this application, various publications are referenced. The disclosures of these publications in their entireties are hereby incorporated by reference into this application in order to more fully describe the state of the art to which this invention pertains.

SUMMARY OF THE INVENTION

It is an object of present invention to provide a DNA segment encoding a receptor protein related to the erbB proto-oncogene family which previously has not been known or even suspected to exist. Further, it is an object of the present invention to develop assays for expression of the RNA and protein products of such genes to enable determining whether abnormal expression of such genes is involved in human cancers. Thus, further objects of this invention include providing antibodies, either polyclonal or monoclonal, specific to a unique portion of the receptor protein; a method for detecting the presence of an erbB-3 ligand that is capable of either activating or down-regulating the receptor protein as well as procedures for purifying the resultant ligand; a method of screening potential ligand analogs for their ability to activate the receptor protein; and procedures for targeting a therapeutic drug to cells having a high level of the receptor protein.

In pursuit of the above objects, the present inventors have discovered a human genomic DNA fragment that is produced by cleavage with the SacI restriction enzyme, has a size of about 9 kbp, and is detectable by nucleic acid hybridization with a probe derived from the v-erbB gene only under reduced stringency hybridization conditions. Thus, this DNA fragment is distinct from those known to encode the epidermal growth factor receptor (EGFR) (i.e., the erbB gene) and from the related erbB-2 gene. Characterization of this DNA fragment after partial purification and molecular cloning showed that the region of v-erbB homology mapped to three exons that encode amino acid sequences having homologies of 64% and 67% to contiguous regions within the tyrosine kinase domains of the EGFR and erbB-2 proteins, respectively. A probe derived from the genomic DNA clone identified cDNA clones of the related mRNA which encode a predicted 148 kDa transmembrane polypeptide with structural features identifying it as a member of the erbB family, prompting designation of the new gene as erbB-3. This gene was mapped to human chromosome 12q11–13 and was shown to be expressed as a 6.2 kb transcript in a variety of normal tissues of epithelial origin. Markedly elevated erbB-3 mRNA levels were demonstrated in certain human mammary tumor cell lines.

The predicted human erbB-3 gene product is closely related to EGFR and erbB-2, which have been implicated as oncogenes in model systems and human neoplasia. The erbB-3 coding sequence was expressed in NIH/3T3 fibroblasts and its product was identified as a 180 kDa glycoprotein, gp180$^{erbB-3}$. Tunicamycin and pulse-chase experiments revealed that the mature protein was processed by N-linked glycosylation of a 145 kDa erbB-3 core polypeptide. The intrinsic catalytic function of gp180$^{erbB-3}$ was uncovered by its ability to autophosphorylate in vitro. Ligand-dependent signaling of its cytoplasmic domain was established employing transfectants which express a chimeric EGFR/erbB-3 protein, gp180$^{EGFR/erbB-3}$. EGF induced tyrosine phosphorylation of the chimera and promoted soft agar colony formation of such transfectants. These findings, combined with the detection of constitutive tyrosine phosphorylation of gp180$^{erbB-3}$ in 4 out of 12 human mammary tumor cell lines, implicates the activated erbB-3 product in the pathogenesis of some human malignancies.

Accordingly, in a principal embodiment, the present invention relates to a DNA segment having a nuclotilde sequence that encodes an erbB-3 gene or a unique portion thereof. This portion of an erbB-3 gene includes at least about 12 to 14 nucleotides which are sufficient to allow formation of a stable duplex with a DNA or RNA segment having sequences complementary to those in this portion of an erbB-3 gene. Further, this unique portion of an erbB-3 gene, of course, has a sequence not present in an erbB or an erbB-2 gene. In other words, the sequence of this portion of an erbB-3 gene differs in at least one nucleotide from the sequence of any other DNA segment. In one embodiment, this DNA segment is exemplified by a human genomic DNA fragment that is produced by cleavage with the SacI restriction enzyme, has a size of about 9 kbp, and is detectable by nucleic acid hybridization with a probe derived from the v-erbB gene only under reduced stringency hybridization conditions, as described in Example 1. By application of the nucleic acid hybridization and cloning methods described in the present disclosure, without undue experimentation, one of ordinary skill in the art of recombinant DNA is enabled to identify and isolate DNA fragments related to the present human DNA fragment comprising a nucleotide sequence that encodes at least a portion of a mammalian erbB-3 gene other than the human erbB-3 gene. Application of the genomic DNA fragment of the erbB-3 gene as a probe in hybridization methods also enables one of ordinary skill in the art to obtain an entire erbB-3 gene, by sequential isolation of overlapping fragments adjoining the present fragment, i.e., by an approach known in the art as chromosome walking.

The present disclosure describes the partial nucleotide sequence of the human genomic 9 kbp SacI DNA fragment, within the region of homology to the v-erbB gene; however, the methods in the present disclosure further enable the isolation and determination of the sequence of the entire 9 kbp human genomic DNA fragment according to the present invention. Accordingly, the present invention further relates to a DNA segment having the nucleotide sequence, or a unique portion thereof, of a human genomic DNA fragment that is produced by cleavage with the SacI restriction enzyme, has a size of about 9 kbp, and is detectable by nucleic acid hybridization with a probe derived from the v-erbB gene only under reduced stringency hybridization conditions, as described in Example 1. By extension of the chromosome walking approach noted above, the present invention further enables one of ordinary skill in the art to determine the sequences of related DNA fragments comprising the complete human erbB-3 gene as well as erbB-3 genes of, for example, mammals other than human.

In the application of the present SacI DNA fragment or any portion thereof as a probe for nucleic acid hybridization, the fragment is amplified, for example, by the in vitro polymerase chain reaction method (PCR; see U.S. Pat. No. 4,683,202; U.S. Pat. No. 4,683,195; and Saiki et al., 1985, *Science* 230:1350–54) or by standard methods of molecular cloning. For example, a clone of the human erbB-3 gene DNA segment according to the present invention is exemplified by a recombinant clone of a normal human thymus DNA fragment, herein designated as the E3-1 genomic clone, having the partial restriction enzyme map defined in FIG. 2 and the partial DNA sequence defined in FIG. 3 and SEQ ID NO:1 of the present application. Isolation and characterization of genomic clone E3-1 is described in Example 2, below.

Analysis of the nucicotide sequences of the human genomic DNA segment according to the present invention reveals that the nuclotilde sequcences encodes three open reading frames bordered by splice junction consensus sequences which define the boundaries between nontranslated intron sequences and the translated exons (shown in FIG. 2 and SEQ ID NO:1). The predicted amino acid sequences of the three exons (SEQ ID NOS:1 and 2) are highly similar to three regions which are contiguous in the tyrosine kinase domains of v-erbB, as well as human EGFR and erbB-2 proteins. Moreover, the predicted amino acid sequences of this human genomic clone are included in a larger open reading frame in complementary DNA (cDNA) clones of an mRNA species that is detected by hybridization of a probe derived from the human genomic DNA clone.

Accordingly, the present invention also relates to a DNA segment having a nucleotide sequence of an erbB-3 gene in which that nucleotide sequence encodes the amino acid sequence of an erbB-3 protein or a unique portion thereof. In other words, the sequence of this portion of an erbB-3 amino acid sequence differs in at least one amino acid residue from the amino acid sequence encoded by any other DNA segment. This portion of an erbB-3 amino acid sequence includes at least about 4 to 6 amino acids which are sufficient to provide a binding site for an antibody specific for this portion of the erbB-3 polypeptide. Further, this unique portion of an erbB-3 amino acid sequence, of course, includes sequences not present in an erbB or an erbB-2 gene. In particular, the present invention relates to such a DNA segment for which this amino acid sequence or unique portion thereof is that of the polypeptide product of the human erbB-3 gene. This DNA segment is exemplified by the human genomic DNA clone E3-1, above, as well as by human cDNA clones designated E3-6, E3-8, E3-9, E3-11 and E3-16, which are described in Example 3 below. A preferred embodiment of this DNA segment that encodes the amino acid sequence of the entire polypeptide product of the human erbB-3 gene is human cDNA clone E3-16 having the nucleotide sequence defined in SEQ ID NO:3 and having the predicted amino acid sequence defined in SEQ ID NOS:3 and 4.

The DNA segments according to this invention are useful for detection of expression of erbB-3 genes in normal and tumor tissues, as described in Example 5 below. Therefore, in yet another aspect, the present invention relates to a bioassay for determining the amount of erbB-3 mRNA in a biological sample comprising the steps of: i) contacting that biological sample with a nucleic acid isolate consisting essentially of a nucleotide sequence that encodes erbB-3 or a unique portion thereof under conditions such that a nucleic acid:RNA hybrid molecule, such as a DNA:RNA hybrid molecule, can be formed; and ii) determining the amount of hybrid molecule present, the amount of hybrid molecule indicating the amount of erbB-3 mRNA in the sample. Findings described in Example 5, below, indicate that increased erbB-3 expression, as detected by this method of this invention, plays a role in some human malignancies, as is the case for the EGFR (erbB) and erbB-2 genes.

Of course, it will be understood by one skilled in the art of genetic engineering that in relation to production of erbB-3 polypeptide products, the present invention also includes DNA segments having DNA sequences other than those in the present examples that also encode the amino acid sequence of the polypeptide product of an erbB-3 gene. For example, it is known that by reference to the universal genetic code, standard genetic engineering methods can be used to produce synthetic DNA segments having various sequences that encode any given amino acid sequence. Such synthetic DNA segments encoding at least a portion of the amino acid sequence of the polypeptide product of the human erbB-3 gene also fall within the scope of the present invention. Further, it is known that different individuals may have slightly different DNA sequences for any given human gene and, in some cases, such mutant or variant genes encode polypeptide products having amino acid sequences which differ among individuals without affecting the essential function of the polypeptide product. Still further, it is also known that many amino acid substitutions can be made in a polypeptide product by genetic engineering methods without affecting the essential function of that polypeptide. Accordingly, the present invention further relates to a DNA segment having a nucleotide sequence that encodes an amino acid sequence differing in at last one amino acid from the amino acid sequence of human erbB-3, or a unique portion thereof, and having greater overall similarity to the amino acid sequence of human erbB-3 than to that of any other polypeptide. The amino acid sequence of this DNA segment includes at least about 4 to 6 amino acids which are sufficient to provide a binding site for an antibody specific for the portion of a polypeptide containing this sequence. In a preferred embodiment, this DNA segment encodes an amino acid sequence having substantially the function of the human erbB-3 polypeptide. As noted above, the predicted erbB-3 polypeptide is a 148 kDa transmembrane polypeptide with structural features identifying it as a member of the erbB receptor family.

The similarity of the amino acid sequence of the present invention with that of an erbB-3 amino acid sequence is determined by the method of analysis defined by the sequence alignment and comparison algorithms described by Pearson and Lipman (Pearson, W. R. & Lipman, D. J., 1988, Proc. Nat. Acad Sci. U.S.A. 85:2444–48). This comparison contemplates not only precise homology of amino acid sequences, but also substitutions of one residue for another which are known to occur frequently in families of evolutionarily related proteins sharing a conserved function.

The present invention further relates to a recombinant DNA molecule comprising a DNA segment of this invention and a vector. In yet another aspect, the present invention relates to a culture of cells transformed with a DNA segment according to this invention. These host cells transformed with DNAs of the invention include both higher eukaryotes, including animal, plant and insect cells, and lower eukaryotes, such as yeast cells, as well as prokaryotic hosts including bacterial cells such as those of *E. coli* and *Bacillus subtilis*. These aspects of the invention are exemplified by recombinant DNAs and cells described in Examples 2, 3 and 6, below.

One particular embodiment of this aspect of this invention comprises a cell, preferably a mammalian cell, transformed with a DNA of the invention, wherein the transforming DNA is capable of being expressed to produce the functional polypeptide of an erbB-3 gene. For example, mammalian cells (COS-1) transformed with the pSV2 gpt vector carrying the E3-16 cDNA are prepared according to well-known methods, (such as those described in U.S. patent application Ser. No. 07/308,302 of Matsui et al., filed Feb. 9, 1989; see also Pierce, J. H. et al., 1988, *Science* 239:628–631; and Matsui, T., Hicidaran M., Miki, T., Popescu, N., La Rochelle, W., Kraus, M., Pierce, J. & Aaronson, S., 1989 *Science* 243:800–804). Briefly, cDNA expression plasmids are constructed by introducing the erbB-3-related cDNA encompassing all the nuclcotides in the open reading frame into the pSV2 gpt vector into which the simian sarcoma virus long-terminal-repeat (LTR) had been engineered as the promoter, as previously described in detail. Transient expression of the erbB-3 gene in such recombinant vectors is achieved by transfection into COS-1 cells.

Stable expression of an erbB-3 gene can also be obtained with mammalian expression vectors such as the pZIP-NEOSVX vector (Cepko, C. L., Roberts B. E. and Mulligan, R. C., 1984, *Cell* 37:1053–62). For example, a eukaryotic expression vector was engineered by cloning the full-length erbB-3 coding sequence derived from cDNA clone E3-16 into the BamzHI site of the pZIPNEOSVX vector DNA adapting the DNA fragments with synthetic oligonucleotides. NIH/3T3 cells were transfected with 1 μg of recombinant expression vector DNA (LTRerbB-3) and selected with the resistance marker antibiotic G418. To detect expression of erbB-3, polyclonal rabbit antiserum was raised against a synthetic peptide (such as amino acid (aa) positions 1191–1205 (SEQ ID NO:5); aa 1254–1268 (SEQ ID NO:6); aa 478–492 (SEQ ID NO:7); aa 1116–1130 (SEQ ID NO:8) and aa 1199–1213 (SEQ ID NO:9)). These peptide epitopes are located intracellularly within the predicted carboxyl terminus of the erbB-3 coding sequence with the exception of aa 478–492, which resides in the extracellular domain of the erbB-3 protein. For example, as shown in FIG. 7, immunoblotting analysis using antiscrum raised against aa 1191–1205 led to detection of the erbB-3 protein (FIG. 7A). The specificity of erbB-3 protein detection was demonstrated by preincubating the antiscrum with the homologous peptide (FIG. 7B). Moreover, the normal 180 kDa erbB-3 protein was specifically detected with the polyclonal antiscrum only in cells transfected with the recombinant erbB-3 expression vector, while control NIH3T3 cells that were not transfected with the vector were negative. There was no cross-reactivity of the above-listed antisera with the related EGFR or erbB-2 proteins overexpressed in NIH/3T3 cells. The stably transfected NIH3T3 cells are useful as erbB-3 receptor protein sources for testing potential candidates for an erbB-3-specific ligand, analysis of the biological activity, as well as generation of monoclonal antibodies raised against the native erbB-3 protein. An erbB-3-specific ligand is identified by detection of autophosphorylation of the erbB-3 receptor protein, stimulation of DNA synthesis or induction of the transformed phenotype of the LTRerbB-3 transfected NIH3T3 cells.

Alternatively, other transformed cell systems are available for functional expression of receptors of the erbB receptor family, for example, a system based on the 32 D cell line, a mouse hematopoietic cell line normally dependent on interleukin-3 (IL-3) for survival and proliferation. Recent studies have established that introduction of an expression vector for the EGFR in these cells leads to effective coupling with EGF mitogenic signal transduction pathways, thereby allowing a ligand of the EGFR to replace IL-3 in supporting survival and growth of the 32 D cells. By employing the known methods described for the EGFR, for example (Pierce, J. H. et al., 1988, supra), the E3-16 cDNA of the present invention is expressed to produce functional receptors in 32 D cells which are then useful for examining the biological function of these erbB-3 receptors, for instance, the specificity of their ligand binding capacity and coupling capacities to secondary messenger systems. Thus, by so using gene expression methods described herein with the DNAs of the present invention, especially the preferred E3-16 cDNA clone, one of ordinary skill in the art, without undue experimentation, can construct cell systems which fall within the scope of this invention, for determining the mechanisms of erbB-3 regulatory processes. Accordingly, the present invention also relates to a bioassay for screening potential analogs of ligands of erbB-3 receptors for the ability to affect an activity mediated by erbB-3 receptors, comprising the steps of: i) contacting a molecule suspected of being a ligand with erbB-3 receptors produced by a cell that yields functional erbB-3 receptors; ii) determining the amount of a biological activity mediated by those erbB-3 receptors; and iii) selecting those analogs which affect the biological activity mediated by the erbB-3 receptors. For example, a compound can be added to a cell having normal or low level erbB-3 phosphorylation. The amount of erbB-3 phosphorylation is then measured and compared to the level prior to adding the compound. The presence of increased activity can then be selected. Alternatively, a cell with high or constitutive erbB-3 phosphorylation can be used to screen for compounds which decrease activity. In addition, an erbB-3 ligand or analogs can be used in this system to screen for the amount of ligand which is necessary to promote or inhibit phosphorylation.

Various standard recombinant systems, such as those cited above as well as others known in the art, are suitable as well for production of large amounts of the novel erbB-3 receptor protein using methods of isolation for receptor proteins that are well known in the art. Therefore, the present invention also encompasses an isolated polypeptide having at least a portion of the amino acid sequence defined in FIG. 4 (SEQ ID NO:4), such as those polypeptides given by SEQ ID NOS:5–9.

The invention further presents results undertaken in an effort to identify and characterize the normal erbB-3 gene product (Examples 6–8). By analysis of an EGFR/erbB-3 chimeric receptor, this invention demonstrates that EGF-dependent activation of the erbB-3 catalytic domain results in a proliferative response in transfected NIH/3T3 cells. Further, the invention shows that some human mammary tumor cell lines exhibit a dramatic elevation of steady state erbB-3 tyrosine phosphorylation, implying functional erbB-3 activation in these tumor cells.

The identification of erbB-3 ligands is of great importance because, for instance, the availability of these ligands will facilitate the complete characterization of erbB-3 biological function as well as development of therapeutic strategies involving the ligands. In particular, the instant observation of functional erbB-3 activation in mammary tumor cells at steady state raises the possibility that a role of erbB-3 in human tumors involves autocrine activation. That is, the simultaneous expression of the ligand by the tumor cell may constitutively activate erbB-3, leading to an uncontrolled proliferative growth response. Accordingly, this invention provides for the detection, purification and characterization of erbB-3 ligands, particularly erbB-3 ligands that are capable of either activating or down-regulating (blocking the activation of) the erbB-3 protein.

The ligand detection and purification method of this invention capitalizes on the erbB-3 expression and activation characteristics in certain cell lines as well as the common property of growth factor receptor tyrosine kinases to rapidly autophosphorylate on tyrosine residues in response to ligand triggering to detect activating or blocking ligand from source containing potential erbB-3 ligands, as described in Example 9. Therefore, in yet another aspect, the present invention relates to a method for detecting the presence of an erbB-3 ligand in a source containing a potential erbB-3 ligand, comprising the steps of a) contacting a first sample of cells from a cell line that expresses erbB-3 protein with the source containing a potential erbB-3 ligand for a time and under conditions sufficient to allow erbB-3 ligand contained in the source to bind to erbB-3 protein to form a triggered sample, wherein the cell line expresses erbB-3 protein having low level intrinsic tyrosine phosphorylation; b) contacting a second sample of cells from the cell line with a control medium (unconditioned serum free medium) for the time and under the conditions as given in step a) above to form a control sample; c) determining the level of erbB-3 activation in the triggered sample and in the control sample; and d) comparing the level of erbB-3 activation in the triggered sample with the level of erbB-3 activation in the control sample, wherein an increase in activation in the triggered sample over the control sample indicates the presence of an erbB-3 activating ligand in the source containing a potential erbB-3 ligand. Alternatively, chimeric receptors, as shown in FIG. 11, can be utilized to screen for erbB-3 ligands. The erbB-3 activation can be ascertained by measuring the level of erbB-3 tyrosine phosphorlation in the triggered sample and in the control sample (an increase in the level of erbB-3 tyrosine phosphorylation correlates with an increase in the level of erbB-3 protein activation); measuring the level of cell growth in the triggered sample and in the control sample (wherein an increase in the level of cell growth correlates with an increase in the level of erbB-3 activation) or measuring the level of DNA synthesis for the cells in the triggered sample and in the control sample (an increase in the level of DNA synthesis for the cells correlates with an increase in the level of erbB-3 activation).

Similarly, the presence of an erbB-3 blocking or inhibiting ligand in a source containing a potential erbB-3 ligand can be detected by a) contacting a first sample of a cell line that expresses erbB-3 protein with the source containing a potential erbB-3 ligand for a time and under conditions sufficient to allow erbB-3 ligand contained in the source to bind to erbB-3 protein to form a blocked sample, wherein the cell line expresses erbB-3 protein having high level intrinsic tyrosine phosphorylation; b) contacting a second sample of the cell line with a control medium for the time and under the conditions as given in step a) to form a control sample; c) determining the level of erbB-3 activation in the blocked sample and in the control sample; and d) comparing the level of erbB-3 activation in the blocked sample with the level of erbB-3 activation in the control sample, wherein a decrease in activation in the blocked sample over the control sample indicates the presence of an erbB-3 blocking ligand in the source containing a potential erbB-3 ligand. Alternatively, chimeric receptors, as shown in FIG. 11, can be utilized to screen for erbB-3 blocking ligands.

In addition, the concentration of various ligands can be utilized to affect the erbB-3 activity. For example, a ligand which promotes erbB-3 activity at low concentrations can be administered or promoted to high concentrations which can inhibit erbB-3 activity.

This invention additionally provides a method of decreasing a biochemical or biological activity mediated by the erbB-3 receptor, comprising blocking the binding of an erbB-3 activating ligand with the erbB-3 receptor. The blocking can be accomplished by an antibody reactive with the ligand binding domain of the erbB-3 receptor or by an erbB-3 blocking ligand. Furthermore, a method of promoting a biochemical or biological activity mediated by the erbB-3 receptor, comprising contacting an erbB-3 activating ligand with the erbB-3 receptor is provided.

This invention also provides a method of detecting the overexpression of erbB-3 in a sample from a subject. The method comprises detecting the amount of erbB-3 in the sample and comparing the amount in the sample to the amount in an equivalent sample having normal expression, the presence of erbB-3 in a greater amount indicating overexpression of erbB-3. By "greater amount" is meant a statistically significant amount. Such amount depends on the conditions utilized and can readily be determined given the teachings set forth herein. Generally, a two-fold or greater increase would be predictive of overexpression. erbB-3 can be detected, for example, by detecting mRNA utilizing Northern hybridization, RNA dot blot, RNA slot blot, or in situ hybridization. erbB-3 can also be detected at the protein level utilizing, for example, Western blots, immunoprecipitation, immunohistochemistry, ELISA, and radioimmunoassay. Once overexpression is detected, the overexpression of erbB-3 can be correlated to a tumor. Such correlation can be used to diagnose a tumor or monitor the progression of a previously diagnosed tumor.

Also provided is a method of detecting the activation of erbB-3 in a test sample from a subject, comprising detecting the presence of phosphorylation of erbB-3, the presence of phosphorylation of erbB-3 indicating the presence of erbB-3 activation in the sample. This method can further comprise comparing the amount of erbB-3 phosphorylation in the test sample to the amount of erbB-3 phosphorylation in a sample from a normal subject and correlating an increase in phosphorylation in the test sample with the presence of a neoplastic condition in the subject. Such correlation can be used to diagnose a tumor or monitor the progression of a previously diagnosed tumor.

This invention further comprises a purified antibody specific for the human erbB-3 polypeptide having the amino acid sequence defined in FIG. 4 (SEQ ID NO:4) or the mature gp180$^{erbB-3}$ protein or a unique portion thereof, such as those polypeptides given by SEQ ID NOS:5–9. In this embodiment of the invention, the antibodies are monoclonal or polyclonal in origin, and are generated using erbB-3 receptor-related polypeptides or peptides from natural, recombinant or synthetic chemistry sources. The term "specific" refers to an erbB-3 antibody capable of binding or otherwise associating nonrandomly with an antigen of erbB-3 such that it does not cross react substantially with other antigens. These antibodies specifically bind to an erbB-3 protein which includes the sequence of such polypeptide. In other words, these antibodies bind substantially only to erbB-3 receptor proteins and not to erbB (EGFR) or erbB-2 proteins. Also, preferred antibodies of this invention bind to an erbB-3 protein when that protein is in its native (biologically active) conformation. For instance, MAb E-31 has been shown to detect the native erbB-3 protein.

Fragments of antibodies of this invention, such as Fab or F(ab)' fragments, which retain antigen binding activity and can be prepared by methods well known in the art, also fall within the scope of the present invention. Further, this invention comprises a pharmaceutical composition of the antibodies of this invention, or an active fragment thereof, which can be prepared using materials and methods for preparing pharmaceutical compositions for administration of polypeptides that are well known in the art and can be adapted readily for administration of the present antibodies without undue experimentation.

These antibodies and active fragments thereof, can be used, for example, for specific detection or purification of the novel erbB-3 receptor. Such antibodies could also be used in various methods known in the art for targeting therapeutic drugs, including cytotoxic agents, to tissues with high levels of erbB-3 receptors, for example, in the treatment of appropriate tumors with conjugates of such antibodies and cell killing agents. Accordingly, the present invention further relates to a method for targeting a therapeutic drug to cells having high levels of erbB-3 receptors, comprising the steps of i) conjugating an antibody specific for an erbB-3 receptor, or an active fragment of that antibody to the therapeutic drug; and ii) administering the resulting conjugate to an individual with cells having high levels of erbB-3 receptors in an effective amount and by an effective route such that the antibody is able to bind to the erbB-3 receptors on those cells.

The antibody of this invention is exemplified by rabbit antisera containing antibodies which specifically bind to erbB-3 protein. Such receptor specific antisera are raised to synthetic peptides representing a unique portion of the erbB-3 amino acid sequence, having six or more amino acids in sequences which are sufficient to provide a binding site for an antibody specific for this portion of the erbB-3 polypeptide. Further, this unique portion of an erbB-3 amino acid sequence, of course, includes sequences not present in an erbB or an erbB-2 amino acid sequence, as predicted by the respective cDNA sequences. The erbB-3 specific antipeptide antibody of the present invention is exemplified by an anti-peptide antibody in polyclonal rabbit antiserum raised against any of the synthetic peptides given in SEQ ID NOS:5–9, which are derived from the predicted sequence of the erbB-3 polypeptide. The specific detection of erbB-3 polypeptide with antiserum raised against the peptide given in SEQ ID NO:5 is illustrated in mammalian cells transformed with an expression vector carrying a human erbB-3 cDNA (see FIG. 7). The antibody of this invention is further exemplified by erbB-3-specific monoclonal antibodies, such as the monoclonal antibody MAb E3-1, which was raised against the recombinantly expressed protein and is capable of detecting the native erbB-3 protein. MAb E3-1 specifically immunoprecipitated the mature 180 kDa erbB-3 protein from LTR-erbB-3 transfectants (FIG. 9A) and did not exhibit cross-reactivity with the EGFR or erbB-2 proteins.

Antibodies to peptides are prepared by chemically synthesizing the peptides, conjugating them to a carrier protein, and injecting the conjugated peptides into rabbits with complete Freund's adjuvant, according to standard methods of peptide immunization. For example, the peptide is synthesized by standard methods (Merrifield, R. B., 1963, *J.*

Amer. Soc., 85:2149) on a solid phase synthesizer. The crude peptide is purified by HPLC and conjugated to the carrier, keyhole limpet hemocyanin or bovine thyroglobulin, for example, by coupling the amino terminal cysteine to the carrier through a maleimido linkage according to well-known methods (e.g., Lerner R. A. et al., 1981, *Proc. Nat. Acad. Sci. USA*, 78:3403). In one standard method of peptide immunology, rabbits are immunized with 100 µg of the erbB-3 peptide-carrier conjugate (1 mg/ml) in an equal volume of complete Freund's adjuvant and then boosted at 10–14 day intervals with 100 µg of conjugated peptide in incomplete Freund's adjuvant. Additional boosts with similar doses at 10–14 day intervals are continued until anti-peptide antibody titer, as determined, for example, by routine ELISA assays, reaches a plateau.

The antibody can be labeled with a detectable moiety or attached to a solid support by methods known in the art to facilitate detection of an antibody/antigen complex. Such a detectable moiety will allow visual detection of a precipitate or a color change, visual detection by microscopy, or automated detection by spectrometry or radiometric measurement or the like. Examples of detectable moieties include fluorescein and rhodamine (for fluorescence microscopy), horseradish peroxidase (for either light microscopy or electron microscopy and biochemical detection), biotin-streptavidin (for light or electron microscopy) and alkaline phosphatase (for biochemical detection by color change). The detection methods and moieties used can be selected, for example, from the list above or other suitable examples by the standard criteria applied to such selections (Harlow and Lane, *Antibodies: A Laboratory Manual*, Cold Spring Harbor Laboratory, Cold Spring Harbor, N.Y. 1988).

Thus, by following the teachings of the present disclosure, including application of generally known immunological methods cited herein, one of ordinary skill in the art is able to obtain erbB-3-specific antibodies and use them in a variety of immunological assays, for example, for diagnostic detection of unusually high or low expression in normal or tumor tissues. Thus, the present invention also relates to a bioassay for detecting an erbB-3 antigen in a biological sample comprising the steps of: i) contacting that sample with an antibody of the present invention specific for an erbB-3 polypeptide, under conditions such that a specific complex of that antibody and that antigen can be formed; and ii) determining the amount of that antibody present in the form of those complexes.

The present invention may be understood more readily by reference to the following detailed description of specific embodiments and the Examples and Figures included therein.

DESCRIPTION OF THE FIGURES

FIG. 3. Nucleotide sequence of the region of v-erbB homology in the human erbB-3 gene derived from human genomic DNA clone E3-1, in the 1.5 kbp region from the EcoRI to the PstI sites. This region contains three open reading frames bordered by splice junction consensus sequences (underlined). The predicted amino acid sequences of the three exons are shown in three letter code below the relevant DNA sequences;

FIG. 7A. Detection of erbB-3 polypeptide with the antiserum. FIG. 7B. Preincubation of the antiserum with homologous peptide. Antibody blocking indicates binding specificity. Lane 1: Selected cultures of NIH3T3 cells transfected with 1 µg LTRerbB-3 expression vector. Lane 2: control NIH3T3 cells;

FIG. 8A. Immunoblot analysis of transfectants with erbB-3 peptide antisera MK4 and MK5 and peptide competition. FIG. 8B. Immunoprecipitation with MK5 antiserum of LTR-erbB-3 transfectants metabolically labeled for 2 h in the presence or absence of glycosylation inhibitor tunicamycin (1 μg/ml).

FIGS. 9A, 9B, 9C and 9D. Immunolocalization of gp180$^{erbB-3}$ on the surface of LTR-erbB-3 cells. FIG. 9A. Immunoprecipitation analysis of metabolically labeled LTR-erbB-3 transfectants with monoclonal antibody E3-1 and a non-immune control. FIG. 9B–D. Indirect immunofluorescence: Formalin-fixed LTR-erbB-3 transfectants were incubated with MAb E3-1 (FIG. 9B) or non-immune IgG (FIG. 9C) and stained with a fluorescein-conjugated secondary antibody (100× original magnification). Indirect immunofluorescence with MAb E3-1 of native LTR-erbB-3 cells (FIG. 9D; 1000× original magnification);

FIGS. 10A, 10B and 10C. Autophosphorylation in vitro and chronic tyrosine phosphorylation in vivo of gp180$^{erbB-3}$, LTR-erbB-3 or control lysates were immunoprecipitated with erbB-3 monoclonal antibody (E3-1) or non-immune IgG (NI). Parallel immunoprecipitates were subjected either to immunoblot analysis with MK4 antiserum (FIG. 10A) or to an immunocomplex kinase assay in the presence of [$^{32}$P]-γATP (FIG. 10B). Tyrosine Phosphorylation in vivo was assayed by immunoprecipitation with monoclonal anti-P-Tyr antibodies followed by immunoblotting with MK4 antiserum (FIG. 10C);

DESCRIPTION OF SPECIFIC EMBODIMENTS

Figure 1A:
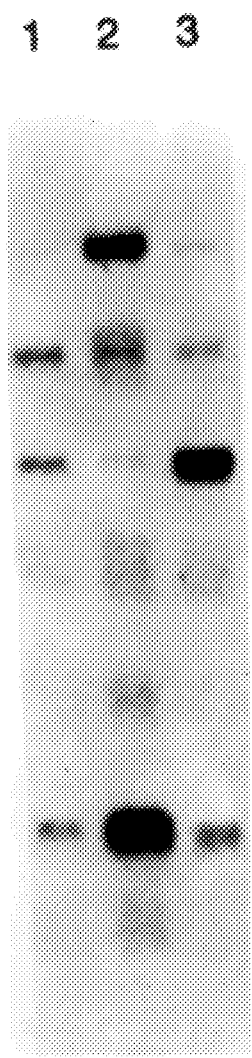
FIG. 1. Detection of v-erbB-related DNA fragments in DNAs from normal human thymus (lane 1), human mammary tumor lines MDA-MB468 (lane 2), and SK-BR-3 (lane 3). Hybridization was conducted at reduced (panel A) or intermediate (panel B) stringency conditions. The arrow denotes a novel 9 kilobase pair (kbp) erbB-related restriction fragment distinct from those of the EGFR gene (erbB) and erbB-2.

As used herein, the terms "polypeptide", "protein", "gene product", "antigen", "receptor", "receptor protein" and the like, when used in reference to erbB-3, encompass the erbB-3 amino acid functional sequence as given in SEQ ID NO:4, the mature erbB-3 glycoprotein, gp180$^{erbB-3}$, and these entities modified by other post-translational modifications, such as glycosylation or tyrosine phosphorylation. However, as is common in the art, the term "erbB-3 polypeptide" typically refers to the sequence as given in SEQ ID NO:4 while the remaining terms typically refer to gp180$^{erbB-3}$.

The identification of a third member of the erbB-EGF receptor family of membrane spanning tyrosine kinases and the cloning of its full length coding sequence is described the Examples herein. The presence of apparent structural domains resembling those of the EGF receptor suggests the existence of an extracellular binding site for a ligand. The structural relatedness of the extracellular domain of the erbB-3 receptor with that of the EGF receptor indicates that one or more of an increasing number of EGF-like ligands (Shoyab, M., Plowman, G. D., McDonald, V. L. Bradley, J. G. & Todaro, G. J., 1989, *Science* 243:1074–1076) interacts with the erbB-3 product. Accordingly, the erbB-3 gene is expected to play important roles in both normal and neoplastic processes, as is known for the EGFR and erbB-2 genes.

Despite extensive collinear homology with the EGF receptor and erbB-2, distinct regions within the predicted erbB-3 coding sequence revealed relatively higher degrees of divergence. For example, its carboxyl terminal domain failed to exhibit significant collinear identity scores with either erbB-2 or EGFR. The divergence at the carboxyl terminus also accounts for minor size differences among the three polypeptides of erbB-3, erbB-2, and EGFR, which possess estimated molecular weights of 148 kilodaltons (kDa), 138 kDa, and 131 kDa, respectively. Within the tyrosine kinase domain, which represents the most conserved region of the predicted erbB-3 protein, a short stretch of 29 amino acids closer to the carboxyl terminus than the ATP binding site differed from regions of the predicted erbB-2 and EGFR coding sequence in 28 and 25 positions, respectively. Such regions of higher divergence in their cytoplasmic domains are likely to confer different functional specificity to these closely related receptor-like molecules. Thus, mutations or other alterations in expression of the erbB-3 gene are likely to cause cancers or genetic disorders different from those associated with such defects in the erbB and erbB-2 genes.

Chromosomal mapping localized erbB-3 to human chromosome 12 at the q11–13 locus, whereas the related EGFR and erbB-2 genes are located at chromosomal sites 7p12–13 and 17p12—21.3, respectively. Thus, each gene appears to be localized to a region containing a different homeobox and a different collagen chain gene locus. Keratin type I and type II genes also map to regions of 12 and 17, respectively, consistent with the different localizations of erbB-3 and erbB-2, respectively. Thus, the DNA segments of the present invention represent novel probes to aid in genetic mapping of any heritable diseases which are associated with chromosomal aberrations in the vicinity of the 12q11–13 locus.

There is evidence for autocrine as well as paracrine effectors of normal cell proliferation. The former are factors that are produced by the same cells upon which they stimulate cell proliferation, whereas the latter factors are secreted by cells other than those that are affected by those factors. However, the inherent transforming potential of autocrine growth factors suggests that growth factors most commonly act on their target cell populations by a paracrine route. The present survey of erbB-3 gene expression indicates its normal expression in cells of epithelial and neuro-ectodermal derivation. Comparative analysis of the three erbB receptor-like genes in different cell types of epidermal tissue revealed that keratinocytes expressed all three genes. In contrast, melanocytes and stromal fibroblasts specifically lacked EGFR and erbB-3 transcripts, respectively. Thus, melanocytes and stromal fibroblasts may be sources of paracrine growth factors for EGFR and erbB-3 products, respectively, that are expressed by the other cell types residing in close proximity in epidermal tissues.

Given that both erbB and erbB-2 have been causally implicated in human malignancy, the present findings (Example 5) that the erbB-3 transcript is overexpressed in a significant fraction of human mammary tumor cell lines indicates that this new member of the EGFR receptor family also plays an important role in some human malignancies.

Characterization of the human erbB-3 gene product, gp180$^{erbB-3}$, shows that it is a transmembrane glycoprotein exhibiting properties characteristic of a receptor-like tyrosine kinase. The recombinant human erbB-3 protein shared identical electrophoretic mobility with the natural erbB-3 product expressed in human breast tumor cell lines. Moreover, both recombinant and endogenously expressed gp180$^{erbB-3}$ was recognized by different antibodies directed against distinct epitopes, such as monoclonal (i.e., Mab E3-1) and peptide antibodies directed against epitopes in the extracellular and carboxyl-terminal domains. The 145 kDa erbB-3 polypeptide precursor conformed with predicted erbB-3 encoded protein following cleavage of its signal sequence. Finally, demonstration of its inherent signaling properties established functional integrity of recombinantly expressed gp180$^{erbB-3}$.

Although the erbB-3 tyrosine kinase domain shares greater than 60% amino acid identity with the EGFR and erbB-2 proteins, single amino acid substitutions differences in highly conserved residues shared among known tyrosine kinases raised a question as to whether erbB-3 harbors intrinsic catalytic activity involved in signal propagation instead of signal attenuation as has been postulated for certain receptor tyrosine kinase-like molecules (Chou et al., Proc. Natl. Acad. Sci. USA 88:4897 (1991)). Most notably, codon 834 within the tyrosine kinase domain predicts asparagine in erbB-3, while aspartate is present at this position in essentially all known protein kinases. Moreover, substitution of asparagine for aspartate in this position abolishes c-kit and v-fps tyrosine kinase activity. The present characterization of the erbB-3 cytoplasmic domain demonstrates not only its catalytic function but also the ability to transduce a mitogenic signal as well. gp180$^{erbB-3}$ demonstrated autokinase activity in vitro and, in some cell lines, tyrosine phosphorylation in vivo. Moreover, EGF-dependent activation of gp180$^{EGFR/erbB-3}$ was associated both with mitogenic signaling and in vivo tyrosine phosphorylation of the chimeric receptor. All of these findings imply that the erbB-3 protein represents a biologically active membrane spanning receptor capable of transducing a mitogenic signal in a ligand-dependent manner. Thus, the erbB-3 gene encodes a membrane spanning molecule possessing all the properties of a functional growth receptor.

Constitutive activation of erbB-3 catalytic activity was demonstrated in LTR-erbB-3 transfectants. These results raise the possibility that NIH/3T3 cells may express an erbB-3 ligand. If so, this putative ligand would unlikely interact with the EGFR, since overexpression of the latter in NIH/3T3 cells is not associated with its chronic tyrosine phosphorylation in the absence of exogenous EGF. This invention further established that EGF neither enhanced in vivo tyrosine phosphorylation of gp180$^{erbB-3}$ nor elicited a mitogenic response in LTR-erbB-3 cells. Additional ligands of the EGF family, including TGFα, amphiregulin, and HB-EGF, have also failed to stimulate gp180$^{erbB-3}$ tyrosine phosphorylation or DNA synthesis in LTR-erbB-3 cells. While a low affinity interaction of known EGF-related ligands for gp180$^{erbB-3}$ cannot be excluded, these findings indicated that erbB-3 and EGFR proteins possess distinct ligand specificities. The ability to trigger the erbB-3 catalytic domain in the EGFR/erbB-3 chimeric molecule should make it possible to more readily identify its substrates as well as to compare them with those of its closely related family members.

Based upon this invention's demonstration that the erbB-3 protein is both catalytically active and can elicit a proliferative response in NIH/3T3 cells, the instant findings of its chronic activation in some human breast tumor cells suggest its contribution to the malignant phenotype in such tumors. Analogous evidence has implicated overexpression associated with gene amplification of both EGFR and erbB-2 in a variety of tumors as well. In such tumors, there is precedence for activation of receptor kinase activity by mechanisms involving autocrine loops as well as genetic alterations affecting regulatory or coding sequences.

Both EGFR and erbB-2 genes have been implicated as oncogenes based upon demonstration of their overexpression and constitutive activation in various human tumors. The results of this invention argue strongly that the most recently identified family member, erbB-3, is activated in some human breast tumors. Overexpression of the erbB-3 protein did not invariably correlate with its chronic tyrosine phosphorylation. Hence, erbB-3 activation may involve autocrine stimulation or subtle genetic alterations. In addition to breast tumors, expression of the erbB-3 transcript has been observed in a wide range of human carcinomas, including colon, lung, kidney, pancreas, and skin. These findings prompt the search for evidence of erbB-3 activation as an oncogene in these other common human cancers.

EXAMPLE 1

Identification of a Human DNA Fragment Related to the erbB-3 proto-oncogene Family In an effort to detect novel erbB-related genes, human genomic DNA was cleaved with a variety of restriction endonucleases and subjected to Southern blot analysis with v-erbB as a probe. Normal mammary epithelial cells AB589 (Walen, K. H. & Stampfer, M. R., 1989, Cancer. Genet. Cytogenet. 37:249–261) and immortalized keratinocytes RHEK have been described previously (Rhim, J. S., Jay, G., Arnstein, P., Price, F. M., Sanford, K. K. & Aaronson, S. A., 1985, Science 227:1250–52). Normal human epidermal melanocytes (NHEM) and keratinocytes (NHEK) were obtained from Clonetics. Sources for human embryo fibroblasts (Rubin, J. S., Osada, H., Finch, P. W., Taylor, W. G., Rudikoff, S., & Aaronson, S. A., 1989, Proc. Nat. Acad. Sci. USA 86:802–806) or mammary tumor cell lines SK-BR-3, MDA-MB468, MDA-MB453, and MDA-MB415 (Kraus, M. H., Popescu, N. C., Amsbaugh, S. C. & King, C. R., 1987, EMBO. J. 6:605–610) have been described. For nucleic acid RNA hybridization, DNA and RNA were transferred to nitrocellulose membranes as previously described (Kraus, M. H., et al., 1987, supra). High stringency hybridization was conducted in 50% formamide and 5×SSC at 42° C. Filters were washed at 50° C. in 0.1×SSC. Reduced stringency hybridization of DNA was carried out in 30% formamide followed by washes in 0.6×SSC, while intermediate stringency was achieved by hybridization in 40% formamide and washing in 0.25×SSC. For the specific results depicted in FIG. 1, DNAs were restricted with SacI and hybridized with probe specific for an oncogenic viral form of the erbB gene, v-erbB, spanning from the upstream BamHI site to the EcoRI site in the avian erythroblastosis proviral DNA (Vennstrom, B., Flashier L., Moscovici, C. & Bishop, J. M., 1980, J. Virol. 36:575–585).

Figure 1B:
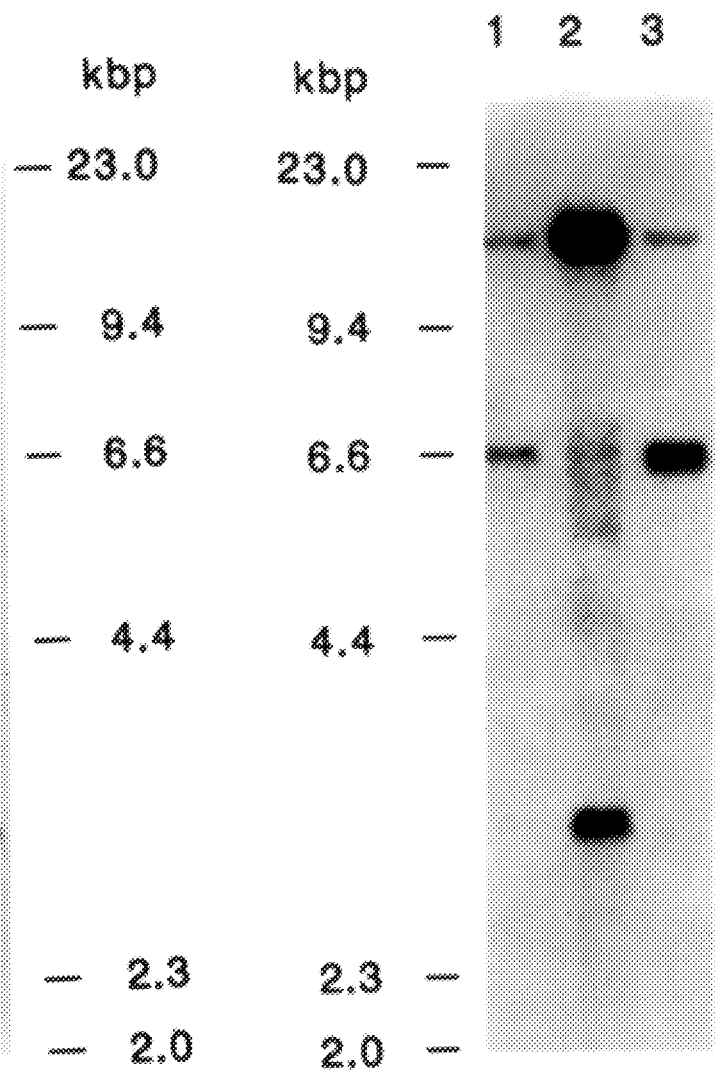

Under reduced stringency hybridization, four SacI restriction fragments were detected. Two were identified as EGFR gene fragments by their amplification in the mammary tumor cell line MDA-MB468 (FIG. 1A, lane 1,2) known to contain EGFR gene amplification and one as an erbB-2 specific gene fragment due to its increased signal intensity in another mammary tumor cell line, SK-BR-3, known to have erbB-2 amplified (FIG. 1A, lane 1,3). However, a single 9 kbp SacI fragment exhibited equal signal intensities in DNAs from normal human thymus, SK-BR-3 and a line with high levels of EGFR, A431 (FIG. 1A). When the hybridization stringency was raised by 7° C., this fragment did not hybridize, whereas EGFR and erbB-2 specific restriction fragments were still detected with v-erbB as a probe (FIG. 1B). Taken together, these findings suggested the specific detection of a novel v-erbB-related DNA sequence within the 9 kbp SacI fragment.

EXAMPLE 2

Cloning of the Human DNA Fragment Related to erbB

For further characterization, a normal human genomic library was prepared from SacI cleaved thymus DNA enriched for 8 to 12 kbp fragments. For convenience, bacteriophage λsep—lac5 was obtained from L. Prestidge and D. Hogness (Stanford University); many other cloning vectors derived from phage λ or other genomes can be used for cloning this DNA fragment according to standard recombinant DNA methods that are well known in the art. Purified phage DNA was subjected to cos-end ligation, restriction with SacI, and fractionation in a continuous 10–40% sucrose gradient. A genomic library was prepared by ligating SacI restriction fragments of normal human thymus DNA in the molecular weight range of 8 kbp to 12 kbp (isolated by sucrose gradient sedimentation) with the purified phage arms. Ten recombinant clones detected by v-erbB under reduced stringency conditions did not hybridize with human EGFR or erbB-2 cDNA probes at high stringency. As shown in the restriction map of a representative clone with 9 kbp insert, the region of v-erbB homology was localized by hybridization analysis to a 1.5 kbp segment spanning from the EcoRI to the downstream PstI site.

Figure 2:
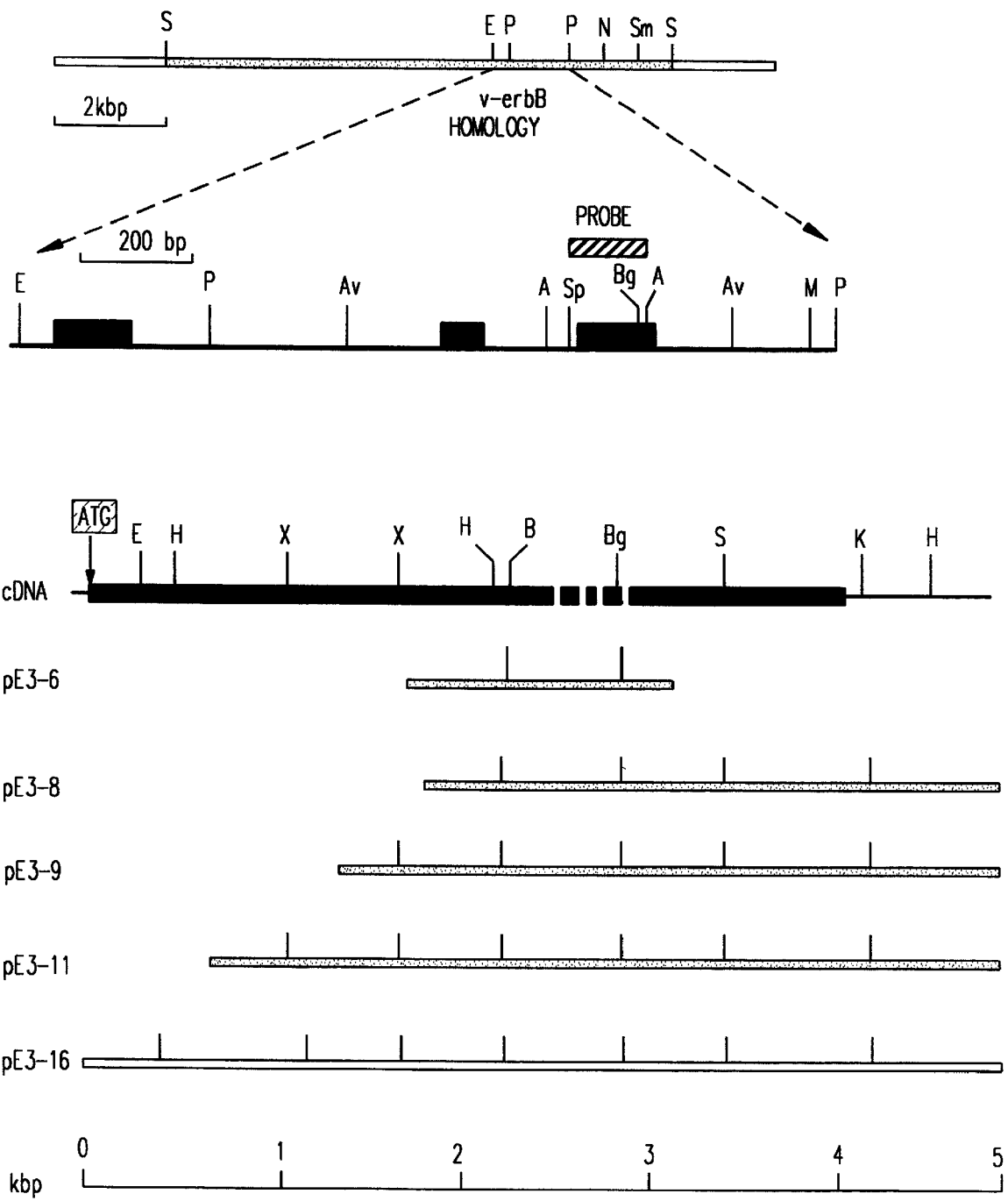
FIG. 2. Genomic and cDNA cloning of erbB-3. The region of (v-erbB) homology within the genomic 9 kbp SacI insert of λE3-1 was subcloned into the plasmid pUC (pE3-1) and subjected to nucleotide sequence analysis. The three predicted exons are depicted as solid boxes. erbB-3 cDNA clones were isolated from oligo dT-primed libraries of mRNAs from normal human placenta (shaded bars) and the breast tumor cell line MCF-7 (open bar). The entire nucleotide sequence was determined for both strands on erbB-3 complementary DNA from normal human placenta and upstream of the 5' XhoI site on pE3-16. The coding sequence is shown as a solid bar and splice junctions of the three characterized genomic exons are indicated by vertical white lines. Solid lines in the cDNA map represent untranslated sequences. Restriction sites: A=AccI, Av=AvaI, B=BamHI, Bg=BglII, E=EcoRI, H=HindIII, K=KpnI, M=MstII, P=PstI, S=SacI, Sm=SmaI, Sp=SpeI.

The nucleotide sequence of a portion of a clone of the novel human genomic DNA fragment related to erbB was determined for both DNA strands by the dideoxy chain termination method (Sanger, F., Nicklen, S. & Coulson, A. R., 1977, *Proc. Nat. Acad. Sci. USA.* 74:5463–67) using supercoiled plasmid DNA as template. The nucleotide sequence was assembled and translated using IntelliGenetics software. Amino acid sequence comparison was performed with the alignment program by Pearson and Lipman (Pearson, W. R. & Lipman, D. J., 1988, supra) as implemented on the computers of the NCI Advanced Scientific Computing Laboratory. Hydrophobic and hydrophilic regions in the predicted protein were identified according to Kyte and Doolittle (Kyte, J. & Doolittle, R. F., 1982, *J. Mol. Biol.* 157:105–132). Nucleotide sequence analysis revealed that the region of v-erbB homology in the 1.5 kbp segment from the EcoRI to the PstI contained three open reading frames bordered by splice junction consensus sequences (FIG. 2). Computerized comparisons of the predicted amino acid sequence of these three open reading frames with other known proteins revealed the highest identity scores of 64% to 67% to three regions which are contiguous in the tyrosine kinase domains of v-erbB, as well as human EGFR and erbB-2 proteins. Furthermore, all splice junctions of the three characterized exons in the new gene were conserved with erbB-2. Amino acid sequence homology to other known tyrosine kinases was significantly lower, ranging from 39% to 46%.

A single 6.2 kb specific mRNA was identified by Northern blot analysis of human epithelial cells using the 150 bp SpeI-AccI exon-containing fragment as probe (FIG. 2). Under the stringent hybridization conditions employed, this probe detected neither the 5 kb erbB-2 mRNA nor the 6 kb and 10 kb EGFR mRNAs. All of these findings suggested that the present work has identified a new functional member of the erbB proto-oncogene family, which tentatively has been designated as erbB-3.

EXAMPLE 3

Cloning and Characterization of cDNAs for the mRNA of the Human erbB-3 Gene

In an effort to characterize the entire erbB-3 coding sequence, overlapping cDNA clones were isolated from oligo dT-primed cDNA libraries from sources with known erbB-3 expression, utilizing gene-specific genomic exons or cDNA fragments as probes. In brief, an oligo dT-primed human placenta cDNA library in λgt11 was obtained from Clontech. MCF-7 cDNA was prepared by first strand synthesis from 5 µg poly A$^+$RNA using an oligo dT containing linker-primer and Mo-MuLV reverse transcriptase, followed by second strand synthesis with DNA polymerase I, RNaseH, and subsequent T4 DNA polymerase treatment. Double-stranded cDNA was directionally cloned into the SfiI site of λpCEV9 using specific linker-adapter oligonucleotides (Miki, T., Matusi, T., Heidaran, M. A. & Aaronson, S. A., 1989, *Gene* 83:137–146; see also, U.S. application Ser. No. 07/386,053 of Miki et al., filed Jul. 28, 1989). Following plaque purification, phage DNA inserts were subcloned into pUC-based plasmid vectors for further characterization. The clones were initially characterized by restriction analysis and hybridization to the mRNA, and were subsequently subjected to nucleotide sequence analysis. Clones designated pE3-6, pE3-8, pE-9, and pE3-11 carrying inserts with molecular weights ranging from 1.3 kbp to 4.3 kbp were isolated from a human placenta library, whereas the pE3-16 clone containing a 5 kbp insert was obtained by screening the MCF-7 cDNA library with the upstream most coding sequence of pE3-11 as a probe. The clones pE3-8, pE3-9, pE3-11, and pE3-16 contained identical 3' ends terminating in a poly A stretch (FIG. 2).

The complete coding sequence of erbB-3 was contained within a single long open reading frame of 4080 nucleotides extending from position 46 to an in-frame termination codon at position 4126. The most upstream ATG codon at position 100 was the likely initiation codon, as it was preceded by an in-frame stop codon at nucleotide position 43 and fulfilled the criteria of Kozak for an authentic initiation codon. The open reading frame comprised 1342 codons predicting a 148 kDa polypeptide. Downstream from the termination codon, multiple stop codons were present in all frames. As shown in SEQ ID NO:4, the deduced amino acid sequence of the erbB-3 polypeptide predicted a transmembrane receptor tyrosine kinase most closely related to EGFR and erbB-2. A hydrophobic signal sequence of erbB-3 was predicted to comprise the 19 amino-terminal amino acid residues. Cleavage of this signal sequence between glycine at position 19 and serine at position 20 would generate a processed polypeptide of 1323 amino acids with an estimated molecular weight of 145 kDa. A single hydrophobic membrane spanning domain encompassing 21 amino acids was identified within the coding sequence separating an extracellular domain of 624 amino acids from a cytoplasmic domain comprising 678 amino acids (SEQ ID NO:4).

The putative erbB-3 ligand-binding domain was 43% and 45% identical in amino acid residues with the predicted erbB-2 and EGFR protein, respectively. Within the extracellular domain, all 50 cysteine residues of the processed erbB-3 polypeptide were conserved and similarly spaced when compared to the EGFR and erbB-2. Forty-seven cysteine residues were organized in two clusters containing 22 and 25 cysteine respectively, a structural hallmark of this tyrosine kinase receptor subfamily (see, for example, Yamamoto, T., Ikawa, S., Akiyama, T., Semba, K., Nomura, N., Miyajima, N., Saito, T. and Toyoshima, K., 1986, *Nature* 319:230–234). Ten potential N-linked glycosylation sites were localized within the erbB-3 extracellular domain. In comparison with the EGFR and erbB-2 proteins, five and two of these glycosylation sites were conserved, respectively. Among these, the site proximal to the transmembrane domain was conserved among all three proteins (SEQ ID NO:4).

Within the cytoplasmic domain, a core of 277 amino acids from position 702 through 978 revealed the most extensive homology with the tyrosine kinase domains of EGFR and erbB-2. In this region 60% or 62% of amino acid residues were identical and 90% or 89% were conserved, respectively. This stretch of amino acid homology coincides with the minimal catalytic domain of tyrosine kinases (Hanks, S. K., Quinn, A. M. & Hunter, T., 1988, *Science* 241:42–52).

Figure 4B:
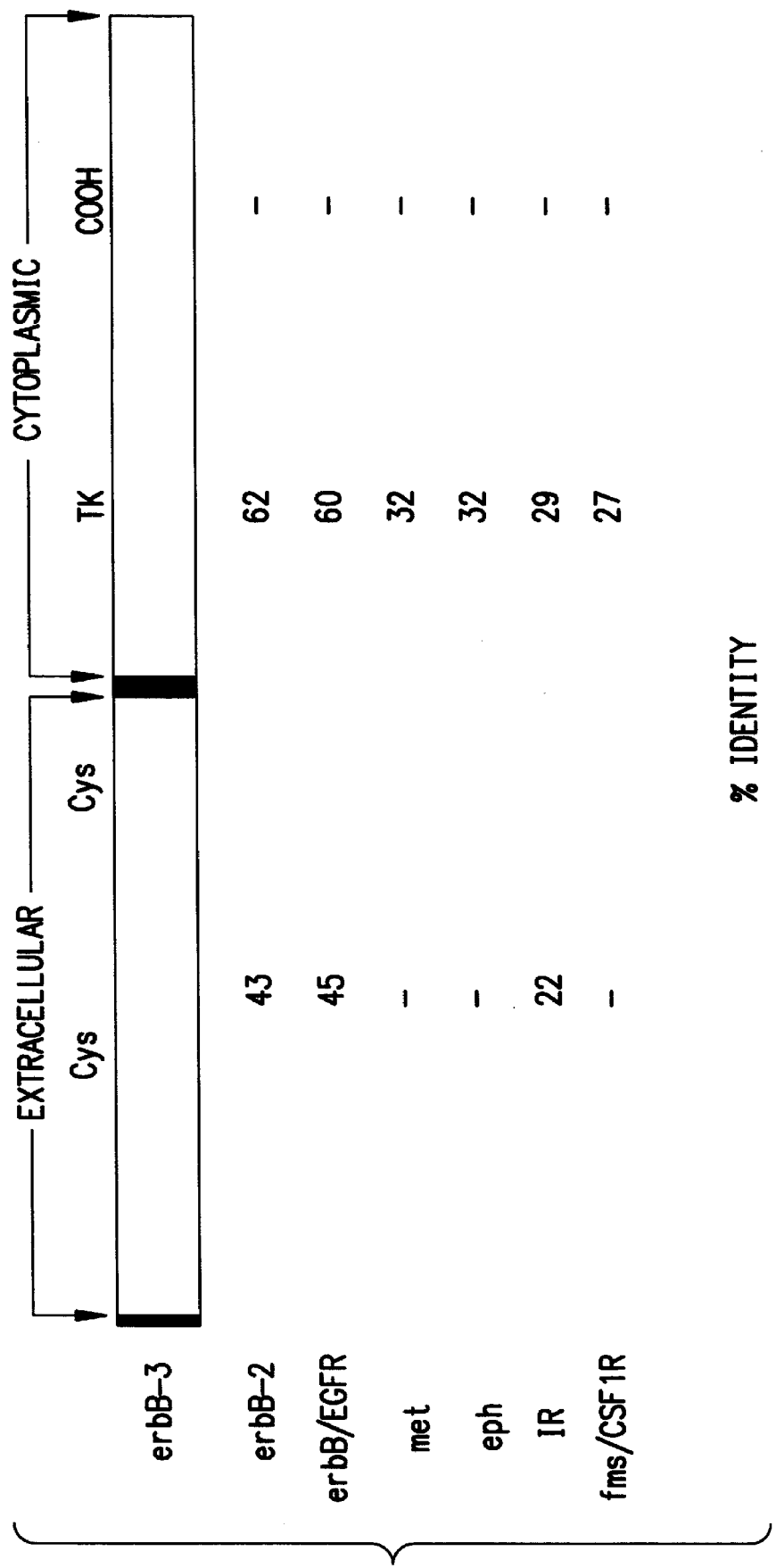
FIG. 4. Comparison of the predicted amino acid sequence of the erbB-3 polypeptide with other receptor-like tyrosine kinases. The amino acid sequence is shown in single letter code and is numbered on the right. The putative extracellular domain (light shading) extends between the predicted signal sequence (solid box) at the amino-terminus and a single hydrophobic transmembrane region (solid box) within the polypeptide. The two cysteine clusters (Cys) in the extracellular domain and the predicted tyrosine kinase domain (TK) within the cytoplasmic portion of the polypeptide are outlined by dark shading. The putative ATP-binding site at the amino-terminus of the TK domain is circled. Potential autophosphorylation sites within the carboxyl terminal domain (COOH) are indicated by asterisks. Potential N-linked glycosylation sites ↪ are marked above the amino acid sequence. The percentage of amino acid homology of erbB-3 in individual domains with erbB-2, EGFR, met, eph, insulin receptor (IR), and fms is listed below. Less than 16% identity is denoted by (–)

There was significantly lower homology with other tyrosine kinases (FIG. 4). The consensus sequence for an ATP-binding site (GxGxxG, Hanks, S. K. et al, 1988, supra) was identified at amino acid positions 716 through 721. This sequence as well as a lysine residue located 21 amino acid residues further toward the carboxyl terminus was conserved between the three erbB-related receptors. Taken together these findings defined the region between amino acid position 702 and 978 as the putative catalytic domain of the erbB-3 protein (SEQ ID NO:4).

The most divergent region of erbB-3 compared to either EGFR or erbB-2 was its carboxyl terminus comprising 364 amino acids. This region showed a high degree of hydrophilicity and the frequent occurrence of proline and tyrosine residues. Among these tyrosine residues, those at positions 1197, 1199, and 1262 matched closest with the consensus sequence for putative phosphorylation sites. The peptide sequence YEYMN (SEQ ID NO:12), encompassing tyrosine 1197 and 1199, was repeated at positions 1260–1264 and was at both locations surrounded by charged residues, providing an environment of high local hydrophilicity. These observations render tyrosines 1197, 1199 and 1262 likely candidates for autophosphorylation sites of the erbB-3 protein.

EXAMPLE 4

Chromosomal Mapping of the Human erbB-3 Gene

Figure 5:
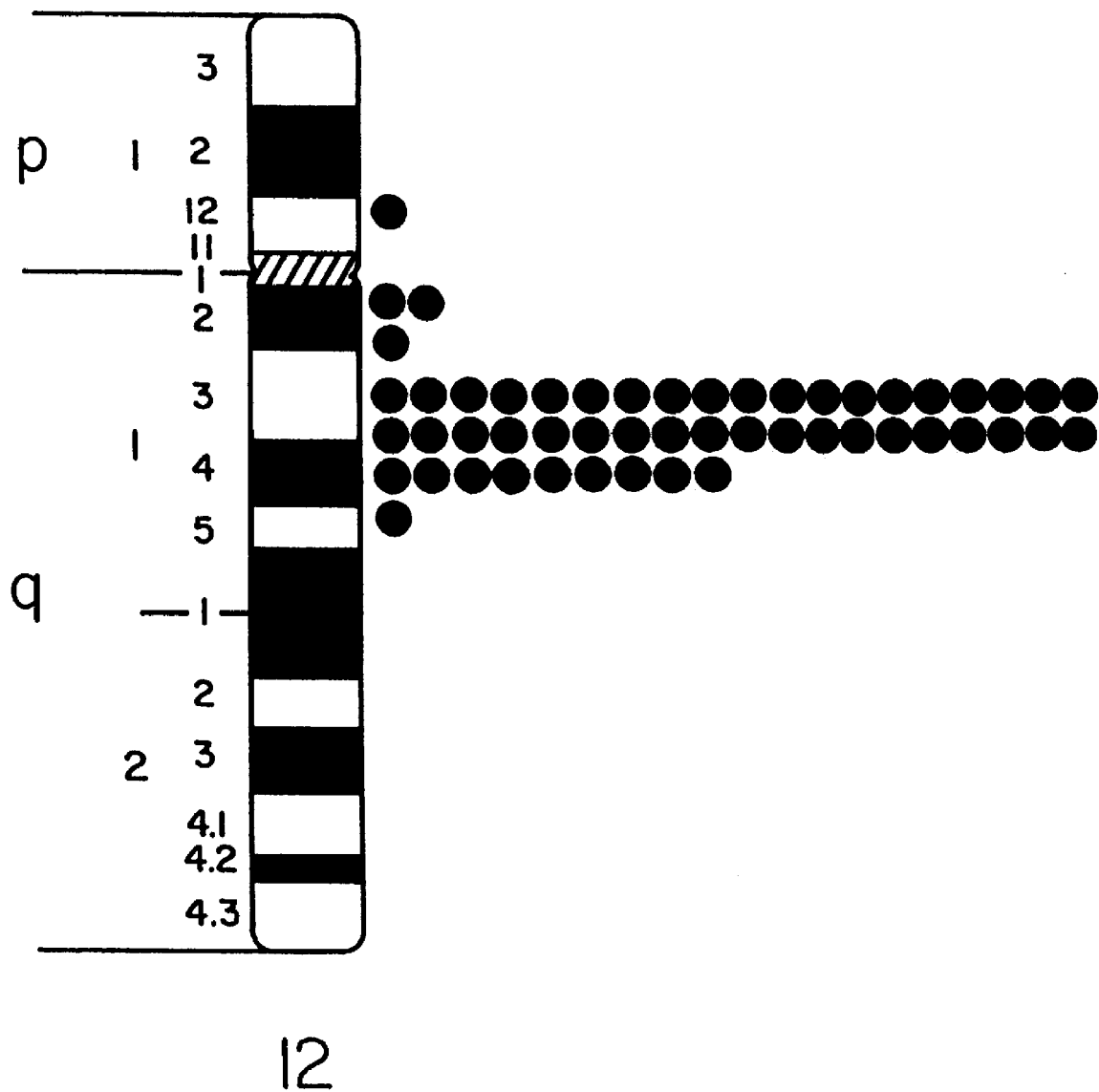
FIG. 5. Assignment of the genomic locus of erbB-3 to human chromosomal locus 12q13. A total of 142 grains were localized on the 400-band ideogram. As depicted in the diagram, specific labeling of chromosome 12 was observed, where 38 out of 51 grains were localized to band q13.

The chromosomal location of the erbB-3 gene was determined by in situ hybridization (Popescu, N. C., King, C. R. & Kraus, M. H., 1989, *Genomics* 4:362–366) with a $^3$H-labeled plasmid containing the amino-terminal erbB-3 coding sequence. A total of 110 human chromosome spreads was examined prior and subsequent to G banding for identification of individual chromosomes. A total of 142 grains was localized on a 400-band ideogram. Specific labeling of chromosome 12 was observed, where 38 out of 51 grains were localized to band q13 (FIG. 5). Thus, the genomic locus of erbB-3 was assigned to 12q13. In this region of chromosome 12, several genes have previously been mapped including the melanoma-associated antigen ME491, histone genes and the gene for lactalbumin. In addition, two proto-oncogenes, int-1 and gli are located in close proximity to erbB-3.

EXAMPLE 5 erbB-3 Expression in Normal and Malignant Human Cells

To investigate its pattern of expression, a number of human tissues were surveyed for the erbB-3 transcript. The 6.2 kb erbB-3 specific mRNA was observed in term placenta, postnatal skin, stomach, lung, kidney, and brain, while it was not detectable in skin fibroblasts, skeletal muscle or lymphoid cell. Among the fetal tissues analyzed, the erbB-3 transcript was expressed in liver, kidney, and brain, but not in fetal heart or embryonic lung fibroblasts. These observations indicate the preferential expression of erbB-3 in epithelial tissues and brain.

ErbB-3 expression was also investigated in individual cell populations derived from normal human epithelial tissues including keratinocytes, glandular epithelial cells, melanocytes, and fibroblasts. For comparison levels of EGFR and erbB-2 transcripts were analyzed. As shown in Table 1, erbB-3 mRNA levels were relatively high in keratinocytes, comparable with those of erbB-2 and EGFR in these cells. Lower, but similar expression levels of each transcript were detected in cells derived from glandular epithelium. These findings are consistent with growth regulatory roles of all three receptor-like molecules in squamous and glandular epithelium. Whereas erbB-2 and EGFR transcripts were also readily observed in normal fibroblasts, the same cells lacked detectable erbB-3 mRNA. In contrast, normal human melanocytes, which expressed both erbB-3 and erbB-2 at levels comparable with human keratinocytes, lacked detectable EGFR transcripts. Thus, the expression patterns of these receptor-like molecules were different in specialized cell populations derived from epidermal tissues.

TABLE 1

| Normal expression pattern of human erbB gene family members | | |
|---|---|---|
| Cell Source of Transcripts | Gene | Relative RNA levels |
| Embryonic fibroblast (M426) | erbB-3 | – |
|  | erbB-2 | + |
|  | EGF-R | + |
| Skin fibroblast (501T) | erbB-3 | – |
|  | erbB-2 | + |
|  | EGF-R | + |
| Immortal keratinocyte (RHEK) | erbB-3 | ++ |
|  | erbB-2 | ++ |
|  | EGF-R | ++ |
| Primary keratinocyte (NHEK) | erbB-3 | + |
|  | erbB-2 | + |
|  | EGF-R | ++ |
| Glandular epithelium (AB589) | erbB-3 | (+) |
|  | erbB-2 | (+) |
|  | EGF-R | (+) |
| Melanocyte (NHEM) | erbB-3 | ++ |
|  | erbB-2 | ++ |
|  | EGF-R | – |

Figure 6A:
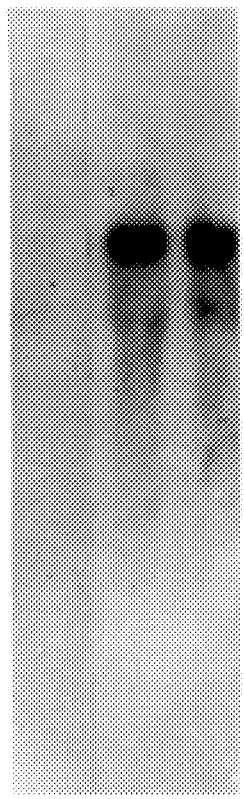
FIGS. 6A and 6B. Elevated erbB-3 transcript levels in human mammary tumor cell lines. A Northern blot containing 10 µg total cellular RNA from AB589 mammary epithelial cells (lane 1), as well as mammary tumor cell lines MDA-MB415 (lane 2) and MDA-MB453 (lane 3) was hybridized with an erbB-3 cDNA probe (FIG. 6A). Following signal decay the same blot was rehybridized with a human β-actin cDNA probe (FIG. 6B) (Gunning, P., Ponte, P., Okayama, H., Engel, J., Blau, H. & Kedes, L., 1983, *Mol. Cell Biol.* 3:787–795)
Figure 6B:
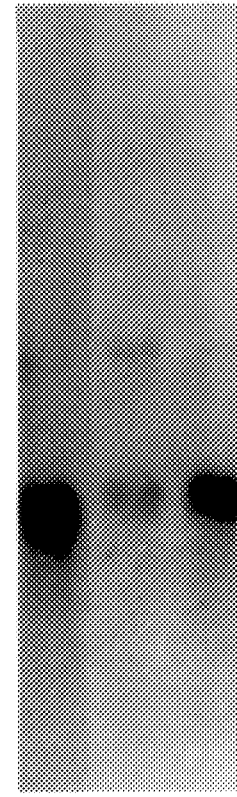
Figure 7A:
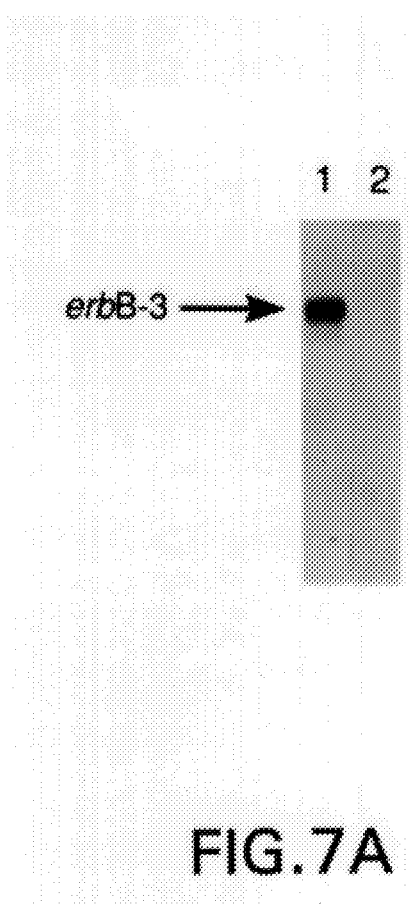
FIG. 7A and 7B. Expression of a human erbB-3 polypeptide in cells transformed by a cDNA segment as detected by an erbB-3-specific anti-peptide antiserum. Cellular lysates (100 µg of each sample) were electrophoresed and transferred to nitrocellulose membranes for analysis by Western blotting.
Figure 7B:
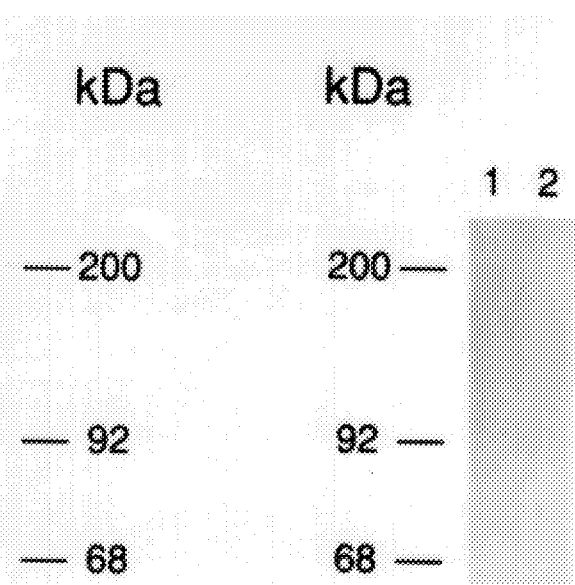

To search for evidence of erbB-3 involvement in the neoplastic process, erbB-3 mRNA levels in a series of human tumor cell lines were surveyed. The erbB-3 transcript was detected in 36 of 38 carcinomas and in of 2 of 12 sarcomas while 7 tumor cell lines of hematopoietic origin lacked measurable erbB-3 mRNA. Markedly elevated levels of a normal-sized transcript were observed in 6 out of 17 tumor cell lines derived from human mammary carcinomas. By Southern blot analysis, neither gross gene rearrangement nor amplification was detected in the cell lines. FIG. 6A shows the results of Northern blot analysis with control AB589 nonmalignant human mammary epithelial cells (lane 1) and two representative human mammary tumor lines, MDA-MB415 (lane 2) and MDA-MB453 (lane 3). Hybridization of the same filter with human β-actin probe (FIG. 6B) verified actual levels of mRNA in each lane. Densitometric scanning indicated that the erbB-3 transcript in each tumor cell line was elevated more than 100 fold above that of the control cell line. Thus, overexpression of this new member of the erbB family, as in the ease of the EGFR and erbB-2 genes, is likely to play an important role in some human malignancies.

EXAMPLE 6

Further Characterization of the normal erbB-3 gene product

The pZIPneo expression vector (Cepko et al, Cell 37:1053 (1984)) was modified by introduction of a unique Sal I cloning site. Following deletion of the Sal I site in the tetracycline resistance gene, the synthetic oligonucleotides 5'-GATCTCGAGTCGAC-3' (SEQ ID NO:10) and 5'-GATCGTCGACTCGA-3' (SEQ ID NO:11) were annealed and ligated into the single Bam HI site to generate pZIPneo$_{sal}$. The erbB-3 open reading frame including 7 nucleotides upstream of the initiation codon and the termination codon (nucleotides 93-4128) was Tinkered with Sal I ends, employing the polymerase chain reaction (PCR) and cloned into pZIPneo$_{sal}$(LTR-erbB). Sense orientation and integrity of the open reading frame were confirmed by restriction analysis as well as nucleotide sequence analysis of cloning boundaries and PCR-amplified regions.

For structural and functional characterization of the erbB-3 gene product, the complete erbB-3 open reading-frame was inserted as given above into the modified ZIPneo vector, placing the cDNA under the transcriptional control of the Moloney murine leukemia virus long-terminal-repeat sequence (LTR-erbB-3). NIHJ/3T3 fibroblasts were transfected with LTR-erbB-3 or LTR-neo control DNA and cultured in the presence or absence of the selective drug G418. Under conditions in which efficient drug resistance ($6\times10^3$ colonies/pmol) was conferred by LTR-erbB-3, no transformed foci were detectable. In contrast, LTR-erbB-2 or EGF-triggered LTR-EGFR induced morphological transformation of NIH-3T3 cells with efficiencies of around $1.2\times10^4$/pmol and $2.3\times10^2$/pmol, respectively.

Figure 8A:
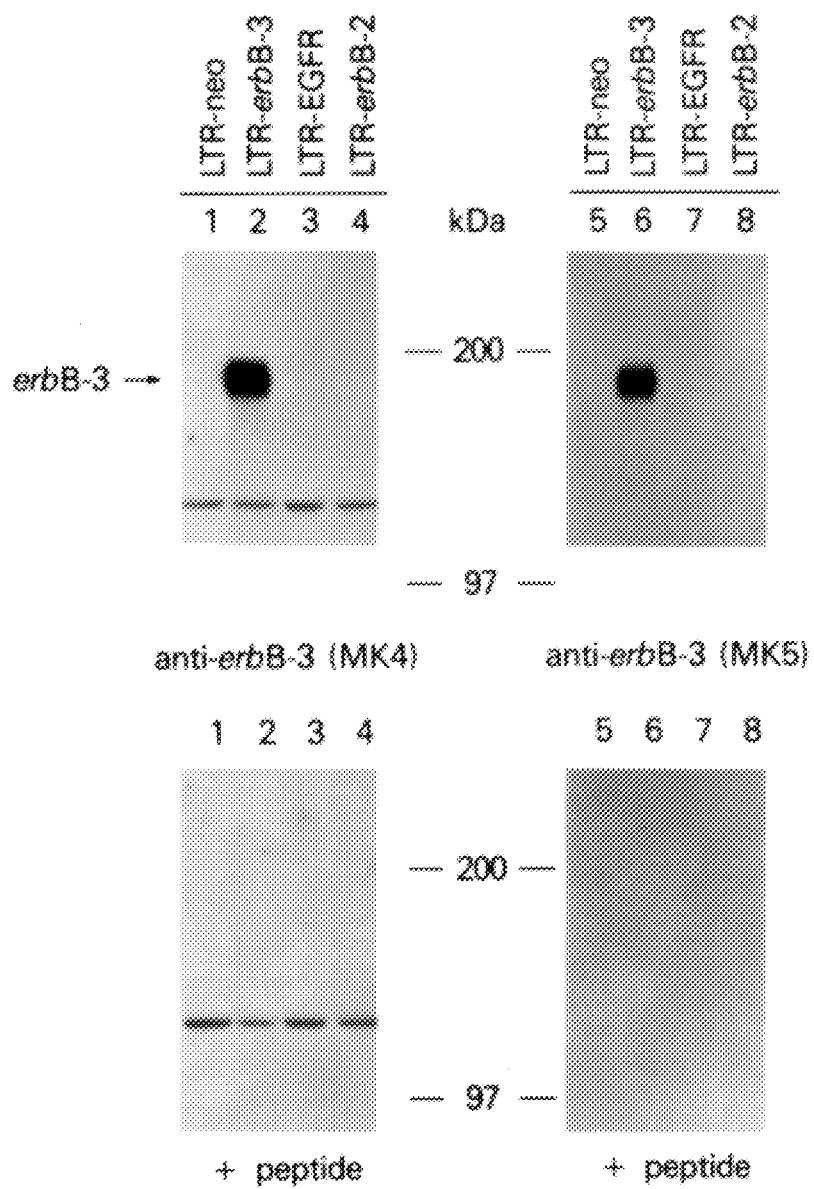
FIGS. 8A and 8B. Characterization of gp180$^{erbB-3}$ recombinantly expressed in NIH/3T3 cells.

To test for expression of the erbB-3 protein, polyclonal rabbit antisera, including MK4 and MK5, were developed against synthetic peptides. MK4 and MK5 were raised against peptides that encompass the residues given in SEQ ID NO:5 and SEQ ID NO:6, respectively, which are within the carboxyl terminus of the predicted erbB-3 product. For immunization, peptides were coupled to thyroglobulin using glutaraldehyde. Immunoblot analysis of lysates from marker-selected LTR-neo and LTR-erbB-3 transfectants revealed a major 180 kDa band only in LTR-erbB-3 cell. This band was independently recognized by both antisera (FIG. 8A). There was no cross-reactivity of either antiserum with the related EGFR or erbB-2 proteins overexpressed in NIH/3T3 cells. Immunoreactivity of either antiserum with the 180 kDa band in LTR-erbB-3 transfectants was competed by the antigenic peptide, while MK4 reactivity with a faint 125 kDa band was not affected by preincubation with peptide (FIG. 8A). These results established specificity of erbB-3 protein detection by both polyclonal antisera. By comparison, the 180 kDa erbB-3 protein migrated distinctly slower than the 170 kDa EGFR and slightly faster than the 185 kDa erbB-2 protein.

Figure 8B:
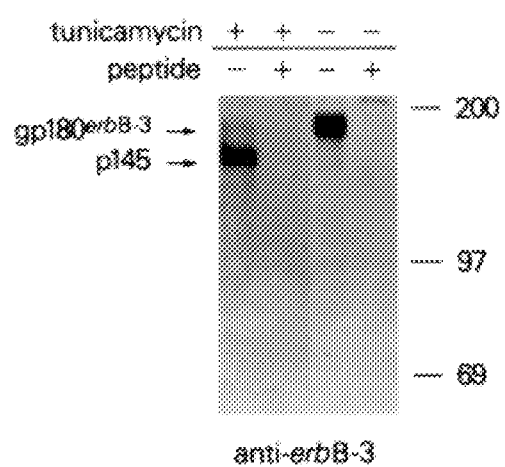
Figure 8C:
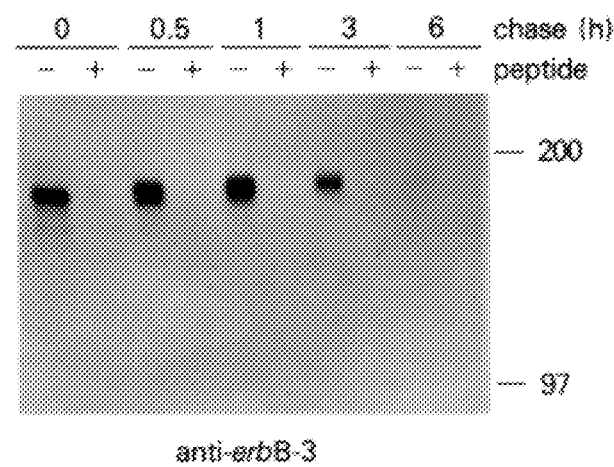
FIG. 8C. Pulse-chase analysis: LTRerbB-3 transfectants were pulse labeled for 15 min with 0.5 mCi each of [$^{35}$S] methionine and [$^{35}$S] cysteine and immediately lysed (0) or chased with 100 μg/ml each of unlabeled methionine and cysteine for the indicated time periods. 1×10$^7$ TCA-precipitable counts were immunoprecipitated from total lysates using MK5 antiserum.

To characterize processing of the erbB-3 protein, we performed immunoprecipitation experiments with MK5 antiserum. Metabolic labeling of LTR-erbB-3 transfectants in the presence or absence of tunicamycin demonstrated that the 145 kDa erbB-3 core polypeptide is modified by N-linked glycosylation (FIG. 8B). Pulse-chase analysis further indicated cotranslational processing, resulting in a predominant 170 kDa precursor protein in addition to faint erbB-3 specific bands of 150 kDa and 160 kDa, following 15 min of pulse-labeling (FIG. 8C). The mature 180 kDa erbB-3 protein appeared after 0.5 h of chase, and the majority was converted into gp180$^{erbB-3}$ by 1 h. By analysis of further time points, we estimate an approximate half-life of 2–3 h (FIG. 8C). Thus, in NIH/3T3 cells, gp180$^{erbB-3}$ exhibits an apparently faster turn-over than the EGFR, for which a biosynthesis time of 3 h and approximate half-life of 3–6 h has been reported.

For immunolocalization of the erbB-3 protein, erbB-3-specific monoclonal antibodies, including MAb E3-1, were raised against the recombinantly expressed protein. BALB/c mice were immunized with live LTR-erbB-3 cells. Somatic cell hybrids were prepared by fusion of immune splenocytes with murine non-secreting myeloma cells NS-1. Hybridoma supernatants were screened for differential immunoreactivity with LTR-erbB-3 but not LTR-neo transfectants by enzyme-linked immunosorbent assay (ELISA) using both live cells or cell extracts as antigen source. Positive hybridoma cell lines were cloned twice by limiting dilution and further characterized by immunoprecipitation and immunofluorescence analysis. One monoclonal antibody, MAb E3-1 (IgG2a isotype), specifically immunoprecipitated gp180$^{erbB-3}$ from LTR-erbB-3 transfectants (FIG. 9A) and did not exhibit cross-reactivity with the EGFR or erbB-2 proteins overexpressed in an NIH/3T3 cell background. Immunofluorescence analysis using a labeled second antibody revealed heterogeneous membrane immunostaining of formalin-fixed LTR-erbB-3 cells using MAb E3-1, but not with a non-specific immunoglobulin of matching isotype (FIG. 9B). MAb E3-1-specific membrane fluorescence of native LTR-erbB-3 cells (FIG. 9B) indicated that gp180$^{erbB-3}$ was expressed at the cell surface, as expected for a membrane-anchored protein.

To investigate its function, we next analyzed the erbB-3 protein for in vitro kinase activity. LTR-erbB-3 and control LTR-neo cell lysates were first immunoprecipitated with E3-1 followed by immunoblot analysis with MK4 antiserum (FIG. 10A). When the same immunoprecipitates were incubated in autokinase buffer containing [$^{32}$P]–γATP, a predominant 180 kDa phosphoprotein was labeled only in immunoprecipitates containing the erbB-3 protein (FIG. 10B). These findings indicated that gp180$^{erbB-3}$ possessed intrinsic protein kinase activity. To assess its enzymatic activity in vivo, LTR-erbB-3 lysates were subjected to immunoprecipitation with phosphotyrosine-specific monoclonal antibodies (anti-P-Tyr) followed by immunoblotting with MK4 antiserum. As shown in FIG. 10C, the erbB-3 protein was recovered from anti-P-Tyr immunoprecipitates, and immunodetection was competed either by phenyl phosphate in the immunoprecipitation or the erbB-3 peptide in Western blot analysis. These findings indicated that recombinant gp180$^{erbB-3}$ expressed in NIH/3T3 cells was chronically phosphorylated on tyrosine residues.

The protein lysates were prepared in Staph A buffer containing the protease inhibitors phenylmethyl sulfonyl fluoride (1 mM) and aprotinin (10 μg/ml; Boehringer Mannheim). For the analysis of phospho-tyrosine proteins, the phosphatase inhibitors sodium orthovanadate (2 mM) and sodium pyrophosphate (10 mM) were added. Immunoblot analysis using peptide antisera was essentially conducted as previously reported. For the detection of phosphotyrosine proteins, membranes were blocked in PBS containing 5% BSA and immunostained with a mixture of monoclonal anti-P-Tyr antibodies (PY20 and PY69; ICN) diluted 1:500 in PBS containing 1% BSA. Filters were washed with PBS containing 0.05% Tween20. Immunoprecipitation was conducted using gammabind G agarose (Pharmacia) to collect the immunocomplexes. The beads were coupled with goat anti-mouse-IgG second antibody (Boehringer Mannheim) in immunoprecipitations using erbB-3 or EGFR monoclonal antibodies. For in vitro kinase assays, 4 mg total lysates were precleared with gammabind G agarose. Following immunoprecipitation, washed immunocomplexes were equilibrated in autokinase buffer containing 40 mM Hepes 7.5, 10 mM $MgCl_2$, and 0.05 Triton. The immunocomplexes were subsequently divided for immunoblot analysis or immunocomplex kinase assay respectively. Autokinase reactions were carried out in 40 µl autokinase buffer containing 20 Ci γATP (3000 ci/mmol) at 25° for 10 min and terminated by addition of SDS containing sample buffer.

EXAMPLE 7

EGF-dependent mitogenic signaling by an EGFR/erb B-3 chimeric receptor

To explore erbB-3 signaling, a chimeric receptor, LTR-EGFR/erbB-3, containing the ligand-binding domain of the closely related EGF receptor (aa 1–682) and the intracellular portion of erbB-3 (aa 681–1342) was engineered. Linearized expression constructs (0.01–10 µg/plate) were transfected into NIH/3T3 cells by calcium phosphate precipitation using 40 µg of calf thymus DNA as carrier. Mass cultures expressing the recombinant proteins were obtained by selection with 750 µg/ml G418. Selected LTR-EGFR/erbB-3 transfectants were enriched for expression of the chimeric protein by preparative FACS sorting using EGFR monoclonal antibody AB-1 (Oncogene Sciences).

Transfection of NIH/3T3 cells with this construct did not result in detectable focus formation either in the presence or absence of EGF. To quantitate expression of the chimeric receptor, selected mass cultures were analyzed for EGF-binding in comparison to NIH/3T3 cells overexpressing the EGFR (LTR-EGFR). Scatchard analysis established around $5.7 \times 10^5$ EGF binding sites/cell for the LTR-EGFR/erbB-3 transfectant as compared to $2.5 \times 10^6$ binding sites/cell for LTR-EGFR transfectant. The LTR-EGFR/erbB-3 transfectant exhibited two populations of binding sites with affinities of 0.11 nM and 5 nM, respectively. The high-affinity sites were in the minority ($2.3 \times 10^4$), and there were $5.5 \times 10^5$ low-affinity binding sites. Similar results were obtained with the wild-type EGFR in LTR-EGFR transfectants, which displayed $1.1 \times 10^5$ high affinity (0.13 nM) and $2.4 \times 10^6$ low affinity receptors (7 nM).

Figure 11:
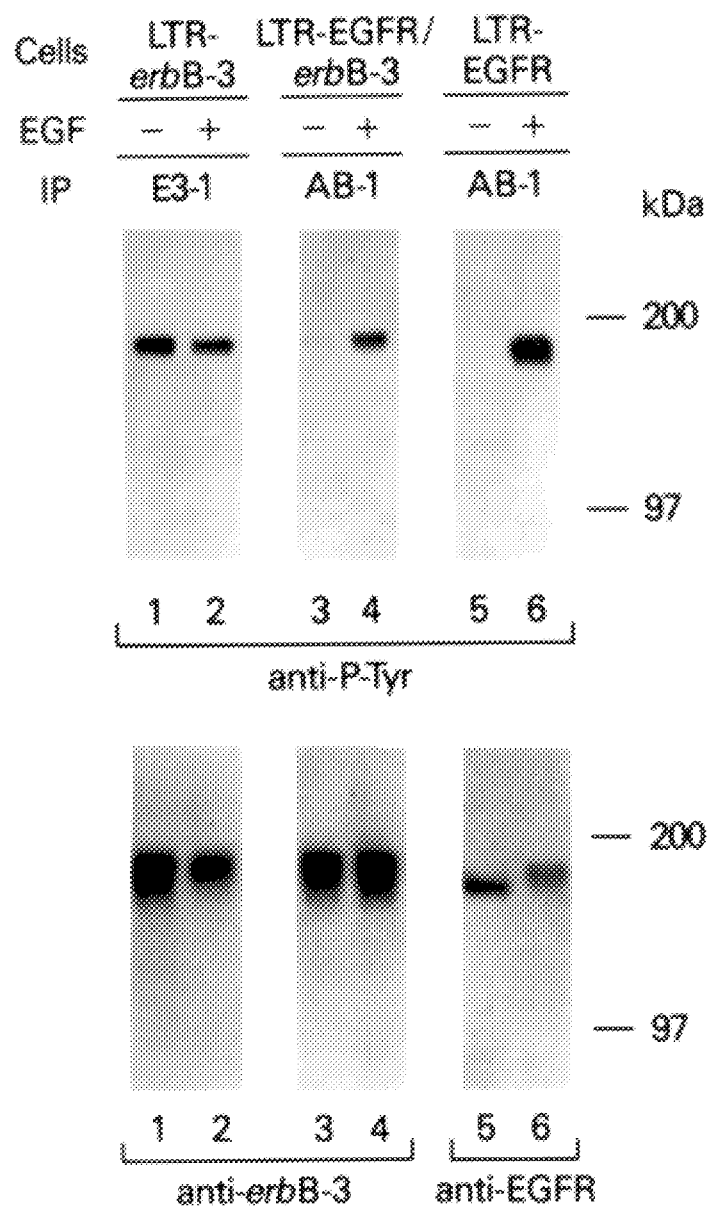
FIG. 11. EGF-dependent tyrosine phosphorylation of an EGFR/erbB-3 chimeric receptor, gp180$^{EGFR/erbB-3}$. Serum-starved LTR-erbB-3, LTR-EGFR/erbB-3, and LTR-EGFR transfectants were triggered with 100 ng/ml EGF. Similar amounts of gp180$^{erbB-3}$, gp180$^{EGFR/erbB-3}$, and EGFR, were immunoprecipitated with erbB-3 (E3-1) or EGFR (AB-1) monoclonal antibodies followed by immunoblot analysis with anti-P-Tyr antibodies or peptide antisera.

To investigate EGF responsiveness of erbB-3 enzymatic activity the in vivo tyrosine phosphorylation of the chimeric receptor in the presence or absence of EGF was compared. This protein, as well as the EGFR and erbB-3 proteins from independent transfectants, was enriched by immunoprecipitation and subjected to immunoblot analysis with either anti-P-Tyr or the appropriate specific antiserum. As shown in FIG. 11, the steady state level of tyrosine phosphorylated $gp180^{erbB-3}$ in NIH/3T3 cells was not altered upon EGF exposure (lane 1,2). The chimeric EGFR/erbB-3 receptor, which was expressed as a 180 kDa protein, $gp180^{EGFR/erbB-3}$ displayed low, but detectable level of tyrosine phosphorylation in serum-free medium (lane 3). However, EGF triggering of the chimera resulted in a substantial increase in tyrosine phosphorylation, demonstrating EGF-dependent activation of erbB-3 catalytic function (lane 4). The wild-type EGFR showed somewhat higher level of EGF-dependent tyrosine phosphorylation under the same conditions (lane 6). Of note, the relative level of $gp180^{erbB-3}$ tyrosine phosphorylation was comparable to that of EGF-activated chimeric receptor expressed at a similar protein level, indicating constitutive activation of erbB-3 catalytic properties in LTR-erbB-3 transfectants.

Whether the erbB-3 catalytic domain was capable of transducing a mitogenic signal was then assessed. When the LTR-EGFR/erbB-3 transfectant was exposed to increasing EGF concentrations, there was a dose-dependent stimulation of DNA synthesis similar to that observed with EGFR overexpressing NIH-3T3 cells. Under the same conditions, neither LTR-neo nor LTR-erbB-3 transfectants showed a significant increase in DNA synthesis even at high EGF concentrations, consistent with previous observations. It should be noted that basal levels of DNA synthesis of the LTRerbB-3 transfectant were 2–3 fold above those of the other transfectants, findings that were reproducible with several independent selected mass cultures.

The biological effects of activated erbB-3 catalytic function were assessed by testing the transfectants for anchorage-independent growth. To test anchorage-independent growth, cell suspensions were seeded at 10-fold serial dilutions in semisolid agarose medium containing growth medium and 0.45% scaplaque agarose (FMC Corp.). Visible colonies comprising >100 cell were scored at 14 days. EGF was added at a concentration of 20 ng/ml. Human mammary tumor cell lines were obtained from the American Type Culture Collection and propagated in Dulbecco's modified Eagle medium containing 10% fetal calf serum.

As shown in Table 2, LTR-neo transfectants failed to exhibit significant soft agar growth in the presence or absence of EGF. In contrast, EGF induced soft agar colony formation with both LTR-EGFR/erbB-3 and LTR-EGFR transfectants. The latter showed a larger colony number (Table 2) as well as colony size (data not shown). By comparison, the LTR-erbB-3 transfectant displayed EGF-independent colony formation with an efficiency similar to that of EGF-activated LTR-EGFR/erbB-3 transfectant (Table 2). All of these findings establish that ligand activation of a chimeric EGFR/erbB-3 receptor causes mitogonic signaling in NIH/3T3 cells and suggest that chronic tyrosine phosphorylation of erbB-3 in LTR-erbB-3 transfectants is associated with constitutive signaling in these cells.

TABLE 2

Anchorage-independent growth of NIH/3T3 transfectants

| NIH3T3 transfectants | # colonies*/$10^4$ cells | |
|---|---|---|
| | −EGF | +EGF |
| LTR-neo | 1 (±1) | 4 (±2) |
| LTR-EGFR | 2 (±2) | 206 (±49) |
| LTR-EGFR/erbB-3 | 7 (±3) | 88 (±16) |
| LTR-erbB-3 | 97 (±20) | 94 (±29) |

*mean (±standard error) of 3 independent assays

EXAMPLE 8

Evidence for activated erbB-3 signaling function in human breast tumor cells

Figure 12:
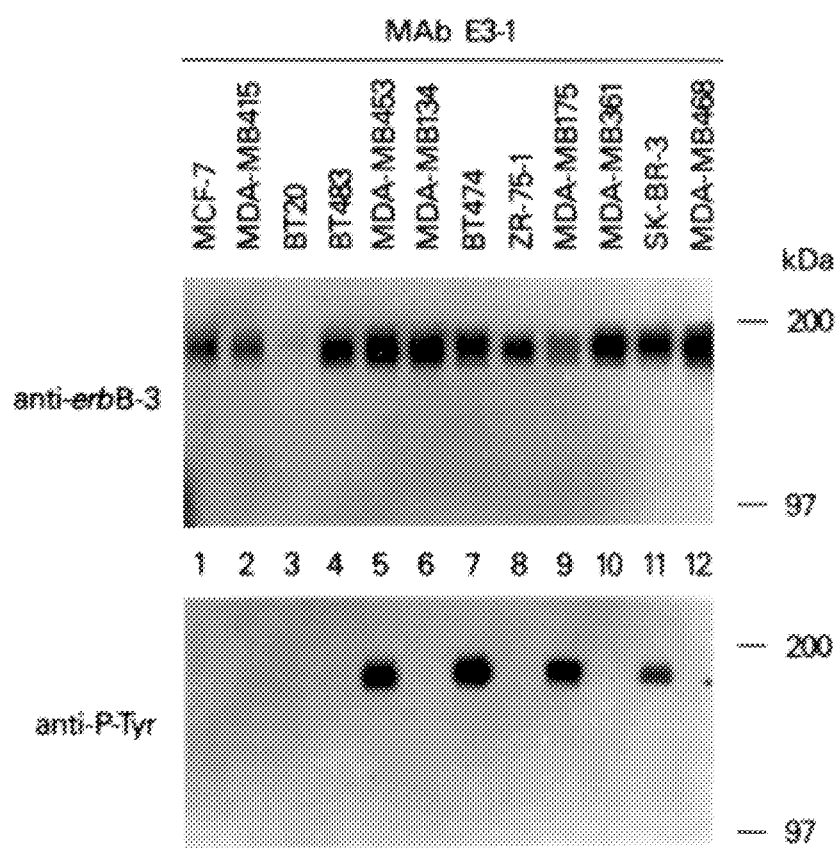
FIG. 12. Activation of gp180$^{erbB-3}$ signaling function in human breast tumor cells. The erbB-3 protein was immunoprecipitated with MAb E3-1 from 1 mg total protein lysate and subjected to immunoblot analysis with erbB-3 peptide antiserum or phosphotyrosine antibodies as indicated.

The availability of erbB-3 specific antibodies made it possible to explore expression and activity of $gp180^{erbB-3}$ in human tumor cells. Based upon our previous evidence for erbB-3 mRNA overexpression in certain breast cancer cell lines, we measured erbB-3 protein levels and tyrosine phosphorylation in such tumor lines, using the procedures given above. Following immunoprecipitation with Mab E3-1, immunoblot analysis with MK4 antiserum revealed the natural human erbB-3 product as a 180 kDa protein. The levels of erbB-3 protein varied markedly along the tumor lines analyzed, with highest expression in BT483, MDA-MB453, MDA-MB134, MDA-MB361, SK-BR-3 and MDA-MB468 (FIG. 12). The lowest levels were observed in BT20 and MDA-MB175 cell lines (FIG. 12), comparable with that expressed by nonmalignant 184B5 mammary epithelial cells (data not shown). Thus, erbB-3 protein expression varied by at least 20–30 fold among the lines tested, consistent with results of transcript analysis (data not shown).

Immunoblot analysis of the same immunoprecipitates with anti-P-Tyr antibodies revealed that tyrosine phosphorylation of the native erbB-3 product was undetectable in 8 of the tumor cell lines, including MDA-MB134, MDA-MB361, and MDA-MB468, which harbored increased erbB-3 levels. In contrast, erbB-3 protein expressed by 4 cell lines, including MDA-MB453, BT474, MDA-MB175, and SK-BR-3, demonstrated readily detectable chronic tyrosine phosphorylation (FIG. 12, lanes 5, 7, 9 and 11). In MDA-MB175, there was no significantly elevated level of erbB-3 protein. Thus, in 4 out of 12 breast tumor cells lines, the $gp180^{erbB-3}$ signaling function was activated at steady state. Whether chronic erbB-3 phosphorylation involves autocrine stimulation or subtle structural alterations, these findings provide evidence for constitutive $gp180^{erbB-3}$ activation in these human breast tumor cells.

EXAMPLE 9

Identification, purification and characterization of erbB-3 ligands

As shown in FIG. 12, the $gp180^{erbB-3}$ that is overexpressed in some human breast tumor cell lines can be either functionally activated or not, depending on the cell line. Further, in some other human breast tumor cell lines, the erbB-3 polypeptide is not overexpressed and, again, can be either activated or not activated. These differences, and the common property of growth factor receptor-like tyrosine kinases to rapidly autophosphorylate on tyrosine residues in response to ligand triggering, can be exploited to identify, isolate and characterize ligands, preferably specific ligands, that can activate or down-regulate erbB-3. The term "erbB-3 ligand" refers to a molecule that binds to the erbB-3 protein, particularly to the extracellular domain of the erbB-3 protein, and can activate ("erbB-3 activating ligand") or down-regulate ("erbB-3 blocking ligand") the biochemical and/or biological activity of the erbB-3 protein. Depending on the concentration of the ligand, a ligand can both activate and down-regulate activity.

A source containing a potential erbB-3 ligand, such as conditioned medium, body fluid extracts, cell extracts, tissue extracts or the like, with or without agents which can modify erbB-3 activity, can be screened for the presence of such a ligand by the ability of the solution, in the case of an activating ligand, to enhance erbB-3 phosphorylation. With respect to screening for an erbB-3 activating ligand, cells from a cell line whose expressed erbB-3 protein contains nonexistent or low level intrinsic tyrosine phosphorylation can be contacted with potential ligand sources or control medium for a time and under conditions sufficient to allow binding of an erbB-3 ligand, if present, to bind to erbB-3. Typically, if an erbB-3 ligand is present, binding will occur within a short time. Thus, the cells are exposed to potential ligand sources or control medium for, preferably, no longer than 30 minutes, most preferably, 10 minutes or less. Appropriate conditions to allow binding of the ligand can be determined by one skilled in the art, such as physiological conditions at 37° C. or the conditions given in FIG. 5 of Holmes et al., Science 256:1205 (1992). erbB-3 modifying agents, if administered, can be present in a concentration between $10^2$ pM and $10^5$ pM. The cell line employed can overexpress erbB-3, such as the mammary tumor cell lines MDA-MB415, MDA-MB134, MDA-MB468, BT483, MDA-MB361, MCF-7 and ZR-75-1, which express an increased amount of the erbB-3 protein with low level intrinsic tyrosine phosphorylation compared to protein amounts and activation levels for corresponding nonmalignant cells. One such potential activating ligand source can be derived from cell lines that not only overexpress erbB-3 but also exhibit high level intrinsic tyrosine phosphorylation, such as MDA-MB453, SK-BR-3, and BT474. In addition, any normal cell which does not overexpress erbB-3 can be utilized, e.g., fibroblasts.

Similarly, with respect to screening for an erbB-3 inhibitory down-regulating ligand, a cell line whose expressed erbB-3 protein contains high level intrinsic tyrosine phosphorylation can be exposed to potential ligand sources or control medium for a time and under conditions sufficient to allow binding of an erbB-3 ligand, if present, to bind to erbB-3. The cell line employed preferably expresses activated erbB-3, such as the mammary tumor cell lines MDA-MB453, SK-BR-3 and BT474. In addition, an activating ligand at higher concentration can be down-regulating. Such activity can be routinely screened given the teaching herein.

The triggering or blocking of erbB-3 activation can be detected by comparing the level of erbB-3 tyrosine phosphorylation in the cell line after exposure to the potential ligand source with the normal level, e.g., the level obtained after exposure to the control medium. For example, in a negative control the cells can be in serum free medium and for activating ligand the conditioned medium is from cell lines with increased erbB-3 that don't have phosphorylation. For instance, to measure erbB-3 specific tyrosine phosphorylation, potentially triggered (or blocked) cells and the control cells are lysed. Using procedures such as those discussed above, the erbB-3 protein is immunoprecipitated with an erbB-3 specific antibody, preferably a monoclonal such as MAb E3-1. The immunoprecipitates are divided and subjected to immunoblot analysis with either antiphosphotyrosine or erbB-3 antibodies. The presence of an erbB-3 activating or blocking ligand can be monitored by a relative increase or decrease, respectively, of phosphotyrosine levels in comparison to the untriggered control. Any increase can be significant, especially a two-fold or greater increase. This ligand-detection system can be used repeatedly throughout the ligand purification procedures so as to monitor protein purification of the erbB-3 ligand to homogeneity.

Alternatively, following exposure of the cell lines to the potential ligand source as discussed above, detection of an erbB-3 activating or blocking ligand can be accomplished by measurement of cell growth and/or mitogenic signals resulting from the activation or inhibition of erbB-3 catalytic activity, using, for example, the procedures given in Example 7 above. An increase in colony number or colony size and/or a dose-dependent increase of DNA synthesis for the cells exposed to the potential ligand relative to those exposed to the control medium correlates with the presence of an activating ligand in the potential ligand source. Conversely, respective decreases correlate with the presence of a blocking ligand in the potential ligand source.

Following the isolation and purification of the erbB-3 ligand, the identity of the ligand can be determined by protein identification methods known in the art, such as amino acid sequencing. Further, the erbB-3 ligand can be molecularly characterized. For instance, similar to the procedures outlined in Holmes et al., *Science* 256:1205 (1992), the nucleic acid sequence that corresponds to the ligand's amino acid sequence, or a partial amino acid sequence corresponding to a portion of the ligand, can be used to design degenerate oligonucleotide probes corresponding to the amino acid sequence or partial sequence. These degenerate oligonucleotides can be used to screen a cDNA library and generate a clone that encodes the precursor of the erbB-3 ligand. Following determination of the coding sequence, related coding sequences can be discovered by screening other libraries.

For purposes of completing the background description and present disclosure, each of the published articles, patents and patent applications heretofore identified in this specification are hereby incorporated by reference into the specification.

The foregoing invention has been described in some detail for purposes of clarity and understanding. It will also be obvious that various changes and combinations in form and detail can be made without departing from the scope of the invention.

What is claimed is:

1. A method for targeting a therapeutic drug to cells having high levels of erbB-3 receptors, comprising:

administering a drug conjugated to an antibody specific for the extracellular domain of gp180$^{erbB-3}$ or an immunogenic fragment thereof, said gp180$^{erbB-3}$ having the amino acid sequence of SEQ ID NO:4 and wherein the antibody is further characterized by not binding erbB-2 or erbB, to an individual with cells having high levels of erbB-3 receptors in an effective amount and by an effective route such that the antibody is able to bind to the receptor on the cells.

2. The method according to claim 1 wherein said immunogenic fragment of gp180$^{erbB-3}$ has the amino acid sequence of SEQ ID NO 7.

* * * * *